United States Patent [19]  
Stephens et al.

[11] Patent Number: 4,769,327  
[45] Date of Patent: Sep. 6, 1988

[54] SECRETION VECTOR

[75] Inventors: Michael A. Stephens, Bedford; Cathy F. Rudolph, Canton; Nancy M. Hannett, Medford; Diane L. Stassi, Belmont; Janice G. Pero, Lexington, all of Mass.

[73] Assignee: Biotechnica International, Inc., Cambridge, Mass.

[21] Appl. No.: 845,864

[22] Filed: Mar. 28, 1986

Related U.S. Application Data

[63] Continuation-in-part of Ser. No. 717,321, Mar. 29, 1985, abandoned.

[51] Int. Cl.$^4$ .................. C12P 21/00; C12N 15/00; C12N 1/20; C12N 1/00
[52] U.S. Cl. .................................. 435/68; 435/172.3; 435/253; 435/320; 935/11; 935/14; 935/29; 935/47; 935/48; 935/73; 935/74; 935/75
[58] Field of Search .................. 435/68, 172.3, 253, 435/317, 320; 935/14, 29, 41, 45, 47, 48, 73, 74, 75

[56] References Cited

U.S. PATENT DOCUMENTS 4,559,300 12/1985 Kovacevic et al. .............. 935/75 X

FOREIGN PATENT DOCUMENTS

| 0114695 | 6/1981 | European Pat. Off. ......... 435/172.3 |
|---|---|---|
| 3021571 | 7/1981 | European Pat. Off. ......... 435/172.3 |
| 0057976 | 8/1982 | European Pat. Off. ............ 435/202 |
| 0063494 | 10/1982 | European Pat. Off. .............. 435/68 |
| 0032238 | 3/1983 | European Pat. Off. ......... 435/172.3 |
| 0127328 | 5/1984 | European Pat. Off. ......... 435/172.3 |
| 0133756 | 6/1985 | European Pat. Off. .............. 435/68 |
| 00341 | 3/1982 | PCT Int'l Appl. ................. 435/253 |
| 2133408 | 12/1980 | United Kingdom .................. 435/68 |
| 2091268 | 2/1981 | United Kingdom .................. 435/68 |
| 2121051 | 4/1982 | United Kingdom ............. 435/172.3 |
| 2069503 | 5/1984 | United Kingdom ............. 435/172.3 |

OTHER PUBLICATIONS

Palva, I. et al., *Proc. Natl Acad Sci*, vol. 79, pp. 5582–5586, 1982.
Stephens, M. et al., *J. Bacteriol*, vol. 158, No. 1, pp. 369–372, 1984, Apr.
Ortlepp, S. A., et al., *Gene*, vol. 23, pp. 267–276, 1983.
Kuhn, H. et al., *J. Bacteriol.*, vol. 149, No. 1, pp. 372–373, 1982.
Bradshaw, R., et al., *Proc. Natl. Acad. Sci.*, vol. 78, No. 6, pp. 3473–3477, 1981.
Inouye, H. et al., *J. Bacteriol.*, vol. 149, No. 2, pp. 434–439, 1982.
Ohmura, K. et al., *Biochem. Biophys. Res. Comm.*, vol. 112, No. 2, pp. 678–683, 1983.
Hofemeister, J. et al., *Mol. Gen. Genet*, vol. 189, pp. 58–68, 1983.
Ferrari, E. et al., *Molec. Gen. Genet.*, vol. 189, pp. 321–325, 1983.
Zuber, P. et al., *Cell*, vol. 35, pp. 275–283, 1983.
Joyet, P. et al., *Fems Microbiology Letters*, vol. 21, pp. 353–358, Mar., 1984.
Sibakov et al., *Eur. J. Biochem.* (1984) 145:567–572.

*Primary Examiner*—Thomas G. Wiseman
*Assistant Examiner*—Jayme A. Huleatt

[57] ABSTRACT

A vector including a DNA sequence encoding a secretory signal sequence substantially identical to the secretory signal encoding sequence of the *Bacillus licheniformis* α-amylase gene; upstream from the signal-encoding sequence, a promoter sequence and a ribosome binding site sequence, transcription of the signal-encoding sequence being under the control of the promoter sequence; and downstream from the signal-encoding sequence, a site for the insertion into the vector of a heterologous DNA sequence, in reading frame with the signal-encoding sequence.

19 Claims, 30 Drawing Sheets

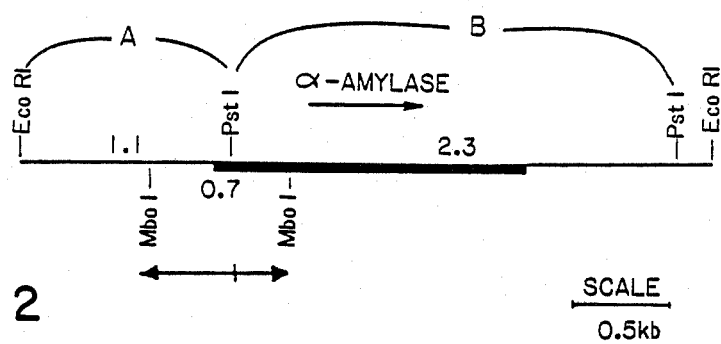

```
5'
AGAGAGGCTATTGAATAAATGAGTAGAAAGCGCCATATCGGCGCTTTTCTTTTGGAAGAAAATATAGGGAAAATGGTAC

-29
TTGACA              TATAAT                                          MET LYS GLN GLN
TTGTTAAAAATTCGGAATATTTATACAATATCATATGTTTCACATTGAAAGGGGAGGAGAATC ATG AAA CAA CAA

-20                    -15                   -10
LYS ARG LEU TYR ALA ARG LEU LEU THR LEU LEU PHE ALA LEU ILE PHE LEU LEU PRO HIS
AAA CGG CTT TAC GCC CGA TTG CTG ACG CTG TTA TTT GCG CTC ATC TTC TTG CTG CCT CAT

MATURE AMYLASE →
 -5       -1  +1         +5                           +10                    +15
SER ALA ALA ALA ALA|ALA ASN LEU ASN GLY THR LEU MET GLN TYR PHE GLU TRP TYR MET
TCT GCA GCA GCG GCG|GCA AAT CTT AAT GGG ACG CTG ATG CAG TAT TTT GAA TGG TAC ATG
        Pst I

+20                   +25                   +30                   +35
PRO ASN ASP GLY GLN HIS TRP LYS ARG LEU GLN ASN ASP SER ALA TYR LEU ALA GLU HIS
CCC AAT GAC GGC CAA CAT TGG AAG CGT TTG CAA AAC GAC TCG GCA TAT TTG GCT GAA CAC

+40                   +45                   +50                   +55
GLY ILE THR ALA VAL TRP ILE PRO PRO ALA TYR LYS GLY THR SER GLN ALA ASP VAL GLY
GGT ATT ACT GCC GTC TGG ATT CCC CCG GCA TAT AAG GGA ACG AGC CAA GCG GAT GTG GGC

+60                   +65                   +70                   +75
TYR GLY ALA TYR ASP LEU TYR ASP LEU GLY GLU PHE HIS GLN LYS GLY THR VAL ARG THR
TAC GGT GCT TAC GAC CTT TAT GAT TTA GGG GAG TTT CAT CAA AAA GGG ACG GTT CGG ACA
                                                                                3'
```

FIG 4

```
       -29                                    -20
B.1.   MET LYS GLN GLN LYS ARG LEU TYR        ALA ARG LEU LEU THR LEU LEU
                 •   •   •                            •   •
B.a.       MET ILE GLN LYS ARG LYS ARG THR VAL SER PHE ARG LEU VAL LEU MET CYS
           -31                                    -20

-10        ⇐ SIGNAL                  -1  | +1 MATURE ⇒
B.1.   PHE ALA LEU ILE PHE LEU LEU PRO HIS SER ALA ALA ALA ALA |ALA ASN LEU ASN
                   •             •   •                        |         •
B.a.   THR LEU LEU PHE VAL SER LEU PRO ILE THR LYS THR SER ALA |    VAL ASN
                        -10                                -1  |    +1

+10                                       +20
B.1.   GLY THR LEU MET GLN TYR PHE GLU TRP TYR MET PRO ASN ASP GLY GLN HIS TRP
         •   •   •   •   •   •   •   •   •   •       •   •   •   •   •   •   •
B.a.   GLY THR LEU MET GLN TYR PHE GLU TRP TYR THR PRO ASN ASP GLY GLN HIS TRP
                                      +10                                +20

+30                                   +40
B.1.   LYS ARG LEU GLN ASN ASP SER ALA TYR LEU ALA GLU HIS GLY ILE THR ALA VAL
         •   •   •   •   •   •       •           •           •   •   •   •   •
B.a.   LYS ARG LEU GLN ASN ASP ALA GLU HIS LEU SER ASP ILE GLY ILE THR ALA VAL
                                   +30

+50
B.1.   TRP ILE PRO PRO ALA TYR LYS GLY THR SER GLN ALA ASP VAL GLY TYR GLY ALA
         •   •   •   •   •   •   •       •   •       •       •   •   •   •
B.a.   TRP ILE PRO PRO ALA TYR LYS GLY LEU SER GLN SER ASP ASN GLY TYR GLY PRO
             +40                                 +50

+60                                  +70            +75
B.1.   TYR ASP LEU TYR ASP LEU GLY GLU PHE HIS GLN LYS GLY THR VAL ARG THR
         •   •   •   •   •   •   •   •   •       •   •   •   •   •   •   •
B.a.   TYR ASP LEU TYR ASP LEU GLY GLU PHE GLN GLN LYS GLY THR VAL ARG THR
             +60                                  +70            +73
```

```
       -29
    5' Met Lys Gln Gln Lys Arg Leu Tyr Ala Arg Leu
    ...ATG AAA CAA CAA AAA CGG CTT TAC GCC CGA TTG
              α-amylase signal sequence Leu Thr Leu Phe Ala Leu Ile Phe Leu Leu
    CTG ACG TTA TTT GCG CTC ATC TTC TTG CTG -1
    Pro His Ser Ala Ala Ala Ala Gly Asp Pro Ser
    CCT CAT TCT GCA GCA GCA GCA GGG GAT CCG TCG
             PstI                    BamHI  linker +5
    Thr Cys Ser Pro Val Leu Glu Asn
    ACC TGC AGC CCT GTT CTG GAA AAC...
        PstI     alkaline phosphatase
```

FIG 8   Amino acid and nucleotide sequences of the fusion of the α-amylase signal sequence to alkaline phosphatase in the vector pNH218.

```
        -29
     Met Lys Gln Gln Lys Arg Leu Tyr Ala Arg Leu
5'...ATG AAA CAA CAA AAA CGG CTT TAC GCC CGA TTG
                   α-amylase signal sequence Leu Thr Leu Leu Phe Ala Leu Ile Phe Leu Leu
     CTG ACG CTG TTA TTT GCG CTC ATC TTC TTG CTG -1  +1
     Pro His Ser Ala Ala Ala  Ala Ala Asn Leu Asn
     CCT CAT TCT GCA GCA GCA  GCA AAT CTT ATT
                 PstI +12
     Pro Ala  Ala  Gln Gly
     CCT GCA  GCT  CAG GGC ...
          PstI   alkaline phosphatase +5
     Gly  Ile Arg Arg Pro Ala
     GGG  ATC CGT CGA CCT GCA
          BamHI  linker   PstI
```

FIG 10 Amino acid and nucleotide sequences of the fusion of the α-amylase signal sequence to alkaline phosphatase in the vector p2/38

FIG 15a

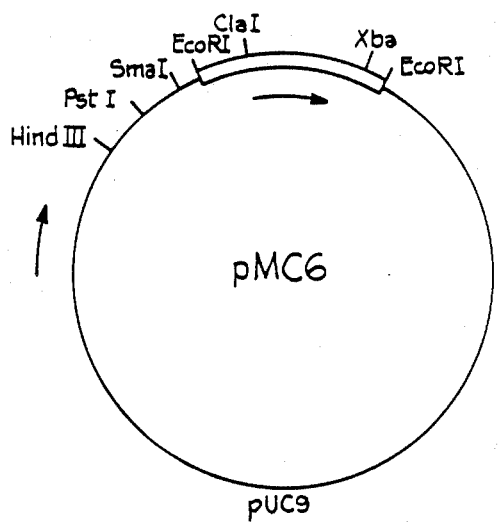

FIG 15b

```
         1     2     3     4     5     6     7    ⑧     9    10
       glu - phe - glu - ser - ser - cys - phe - gly - gly - arg - ile - asp - arg- 5'- A-A-T-T-C-G-A-A-T-C-C-A-G-C-T-G-T-T-T-C-G-G-C-G-G-G-A-G-A-A-T-C-G-A-T-A-G-A-
    EcoRI           PvuII                                      ClaI
3'-         G-C-T-T-A-G-G-T-C-G-A-C-A-A-A-G-C-C-G-C-C-C-T-C-T-T-A-G-C-T-A-T-C-T 11    12    13    14    15    16    17    18    19    20
       ile - gly - ala - gln - ser - gly - leu - gly - cys - asn A-T-C-G-G-C-G-C-C-C-A-A-T-C-A-G-G-C-C-T-T-G-G-G-T-G-T-A-A-C
        NarI                StuI
   T-A-G-C-C-G-C-G-G-G-T-T-A-G-T-C-C-G-G-A-A-C-C-C-A-C-A-T-T-G 21    22    23    24
       ser - phe - arg - tyr - ter - ter T-C-T-T-T-C-C-G-T-T-A-C-T-A-A-T-G-A-T-C-T-A-G-A-G            -3'
                                         XbaI        EcoRI
   A-G-A-A-A-G-G-C-A-A-T-G-A-T-T-A-C-T-A-G-A-T-C-T-C-T-T-A-A   -5'
```

```
                          Nde I
5'        G-C-A-G-C-G-G-C-A-T-A-T-G-C-T-G-A-C-G-C
3'  A-C-G-T-C-G-T-C-G-C-C-G-T-A-T-A-C-G-A-C-T-G-C-G-C-T-A-G
    Pst I                                        Sau3A I
```

FIG. 31(a) Synthetic DNA linker to create "nature-identical" fusion of α-amylase signal sequence to GRF.

HUMAN GROWTH HORMONE RELEASING FACTOR

```
       0      1     2     3     4     5     6     7     8     9    10
      met - tyr - ala - asp - ala - ile - phe - thr - asn - ser - tyr -
|G-A-A-T-C|-A-T-G-T-A-T-G-C-T-G-A-C-G-C-|G-A-T-C|-T-T-T-A-C-C-A-A-C-T-C-T-T-A-T-
|EcoRI    |
|C-T-T-A-A-G|-T-A-C-A-T-A-C-G-A-C-T-G-C-G|-C-T-A-G|-A-A-A-T-G-G-T-T-G-A-G-A-A-T-A-

11    12    13    14    15    16    17    18    19    20
     arg - lys - val - leu - gly - gln - leu - ser - ala - arg -
     C-G-C-A-A-A-G-T-T-C-T-G-G-G-C-C-A-G-C-T-T-T-C-C-G-C-T-C-G-T-
     G-C-G-T-T-T-C-A-A-G-A-C-C-C-G-G-T-C-G-A-A-A-G-G-C-G-A-G-C-A-

21    22    23    24    25    26    27    28    29    30
     lys - leu - leu - gln - asp - ile - met - ser - arg - gln -
     A-A-G-C-T-T-C-T-C-C-A-A-G-A-T-A-T-T-A-T-G-T-C-G-C-G-T-C-A-G-
     Hind III
     T-T-C-G-A-A-G-A-C-G-T-T-C-T-A-T-A-A-T-A-C-A-G-C-G-C-A-G-T-C-

31    32    33    34    35    36    37    38    39    40
     gln - gly - glu - ser - asn - gln - glu - arg - gly - ala -
     C-A-A-G-G-T-G-A-A-A-G-C-A-A-C-C-A-G-G-A-A-C-G-C-G-G-C-G|C-T-|
                                                            |Xbo I|
     G-T-T-C-C-A-C-T-T-T-C-G-T-T-G-G-T-C-C-T-T-G-C-G-C-C-G-C|G-A-|

41    42    43    44    45    46
     arg - ala - arg - leu - ter - ter
     |C-G-A-G|-C-A-C-G-T-C-T-G-T-A-A-T-G-A-|G-A-A-T-T-C|
                                            |EcoRI    |
     |G-C-T-C|-G-T-G-C-A-G-A-C-A-T-T-A-C-T-|C-T-T-A-A-G|
```

FIG. 31(b) GRF gene.

SECRETION VECTOR

BACKGROUND OF THE INVENTION

This application is a continuation-in-part of an application entitled "Secretion Vector", U.S. Ser. No. 717,321, filed Mar. 29, 1985, now abandoned.

This invention relates to the use of genetic engineering to produce desired polypeptides (as used herein, "polypeptides" means any useful chain of amino acids, including proteins and peptides).

Production of heterologous polypeptides in bacteria often requires that extensive purification procedures be used to isolate the polypeptide from the complex mixture of proteins and other molecules present in the bacteria. Additionally, the intracellular environment is not always conductive to the spontaneous formation of disulfide bonds which are frequently required to maintain the stability and activity of certain enzymes and other proteins. As a consequence, biochemical modification may be required in some instances to renature and activate the proteins thus obtained.

It is thus desirable that heterologous polypeptides be secreted from bacteria into the culture medium, from which purification is simpler and less costly.

Bacteria of the genus Bacillus are known to secrete some endogenous proteins. One mechanism of Bacillus secretion involves DNA sequences at the 5' ends of the structural genes, which effect the secretion of the protein from the cell. Such a sequence generally encodes a short hydrophobic "signal sequence," an amino acid chain at the N-terminal end of the protein, which enters through the cellular membrane and carries the protein out of the cell, and in the process is cleaved off.

Palva UK Patent Application GB No. 2,091,268 describes recombinant plasmids containing the regulatory and secretory signals of the α-amylase gene of *Bacillus amyloliquefaciens*, and the structural genes for α-2-interferon or beta-lactamase; the plasmids were used to transform *B. subtilis* for the synthesis and secretion of these proteins.

Hardy et al. EP Application No. 82302157.1 describes a cloning vector for the production of hepatitis B core antigens in *Bacillus subtilis*. Hardy et al. say:

> None of the above-described polypeptides was observed to have been secreted extracellularly of the Bacillus host transformed with the plasmids described in Examples I-II. However, such behavior was expected, because none of the DNA sequences that coded for such products included or were fused to a DNA signal sequence that would be recognized and correctly processed for secretion by Bacillus hosts. Signal sequences that are recognized by Bacillus hosts are known. They include, for example, the signal sequence for the penicillinase gene of *Bacillus licheniformis* (determined by H. Schaller, private communication) and the signal sequence for the gene coding for α-amylase. Therefore, construction of a plasmid to provide a foreign gene with such signal sequence will permit secretion of the foreign gene's product from the Bacillus host. Such constructions do not depart from the scope of the invention and should be considered as an integral part thereof.

Chang International Application No. PCT/US84/00341 describes the production and secretion of heterologous proteins in *B. subtilis* transformed with vectors containing the structural genes for the proteins, adjacent a modified signal sequence derived from the beta-lactamase gene of *B. licheniformis*.

SUMMARY OF THE INVENTION

In general, the invention features a vector including a secretory signal-encoding DNA sequence substantially identical to the secretory signal-encoding sequence of the *B. licheniformis* α-amylase gene. Upstream from the signal-encoding sequence are a promoter sequence and a ribosome binding site sequence, transcription of the signal-encoding sequence being under the control of the promoter sequence. Downstream from the signal-encoding sequence is a site for the insertion of a desired heterologous DNA sequence, in-frame with the signal-encoding sequence. ("Heterologous", as used herein, means a DNA sequence derived from an organism other than the host organism, or from a different location in the host organism, or a synthetic DNA sequence.) Placement of the heterologous DNA is such that transcription and translation of the signal-encoding sequence and heterologous DNA are under the control of the promoter and ribosome binding site. Preferably, the promoter and ribosome binding site sequences are substantially identical to naturally occurring Bacillus promoter and ribosome binding site sequences, e.g., those naturally functionally associated with the *B. licheniformis* α-amylase gene, or with a gene involved in Bacillus sporulation, e.g., the spoVG gene.

The invention provides the ability to produce in bacteria desired polypeptides and to effect the secretion of such polypeptides from the host bacterial cells. In preferred embodiments, the bacteria are Gram positive bacteria, such as Bacillus and Streptomyces, or Gram negative bacteria such as *E. coli*. Both the ability to employ bacteria, such as Bacillus bacteria and Streptomyces bacteria, as the host bacteria, and to effect secretion, offer significant advantages.

The use of Gram positive bacteria as host cells overcomes problems associated with the use of Gram negative bacteria such as *E. coli*. (Although, as mentioned above, the vector of this invention may also be used to produce desired polypeptides in *E. coli*.) Bacillus bacteria do not produce endotoxins, generally are non-pathogenic, and there is considerable industrial experience concerning the conditions required for their optimal fermentation. Perhaps more importantly, their simple single-membrane structure allows true polypeptide secretion into the culture medium; this secretion is made possible by the signal sequence encoded by the vectors of the invention. Secretion into the medium greatly simplifies purification of the desired polypeptide (from which the signal is cleaved during secretion). Secretion also permits the formation of disulfide bonds, which are essential for the biological activity of many proteins.

One heterologous protein whose expression and secretion can be widely useful is the enzyme alkaline phosphatase, whose activity depends on the formation of disulfide bonds, and which causes a color change when bacteria secreting the enzyme are plated onto substrate-containing indicator plates (Wright et al. (1983) J. Cell Biochem. Suppl. (Part 7B) 346). A desired gene can be fused to be alkaline phosphatase gene, and expression monitored by observing enzymatic activity. Host and vector mutations which result in increased levels of protein expression and secretion can also be detected using this system.

Other polypeptides which can be expressed and secreted according to the invention are the mammalian (particularly human) atrial polypeptides having natriuretic activity, and derivatives and analogs thereof. The human polypeptide has been reported in the literature under a variety of names, and as having a range of amino acid chain lengths; these are given in Palluk et al. (1985) Life Sciences 36, 1415. We use herein the nomenclature of FIG. 1 of that paper, which names the precursor molecule human atrial natriuretic factor, and names three smaller derivatives of the molecule Atriopeptin I, Atriopeptin II, and Atriopeptin III ("APIII"). These polypeptides can be administered to human patients to control hypertension and regulate serum sodium and potassium levels.

Other peptides which can be expressed and secreted according to the invention are the potentially therapeutically useful mammalian peptide growth hormone releasing factors (referred to as "GRF"). The amino acid sequence of human GRF is given in Guillemin et al. (1982) Science 218, 585.

Rather than using only the DNA sequence encoding the B. licheniformis α-amylase secretory signal, all or a portion of the α-amylase structural gene can be included in the vectors of the invention as well, and the desired heterologous DNA inserted at the C-terminus of the structural gene, at the N-terminus adjacent the signal-encoding sequence, or anywhere in between.

In another aspect, the invention features a method for obtaining, from a heterogeneous population of DNA fragments, a DNA fragment exhibiting promoter activity in Gram positive bacteria, by providing a plurality of identical vectors, each capable of replicating in Gram positive bacterial cells and including an α-amylase gene including a secretory signal-encoding sequence therefor preceded by a ribosome binding site, the vector having, upstream from and near to (within about 50 bp) the ribosome binding site, a restriction site for the insertion of a DNA fragment, there being no promoter on the vector positioned to control the transcription of the α-amylase gene, inserting the DNA fragments into the restriction site, transforming Gram positive bacteria with the vectors, and testing the transformed bacteria for α-amylase secretion, bacteria secreting α-amylase comprising bacteria which carry a vector containing a DNA fragment exhibiting the promoter activity.

In another aspect, the invention features apparatus for testing bacteria for α-amylase secretion, including a container having a bottom layer and a top layer, the bottom layer containing solidified nutrient medium substantially free of any indicator substance for α-amylase, and the top layer containing solidified nutrient medium containing an indicator substance for α-amylase.

In preferred embodiments, the vector of the invention can be integrated into a bacterial chromosome, amplified, and stably maintained in the absence of drug-selection. Alternatively, the vector can carry a bacterial replicon allowing it to be replicated autonomously in Gram positive bacteria such as Bacillus or Streptomyces or Gram negative bacteria such as E. coli.

Other features and advantages of the invention will be apparent from the following description of the preferred embodiment thereof, and from the claims.

DESCRIPTION OF THE PREFERRED EMBODIMENTS

The drawings will first briefly be described.

Drawings

FIG. 2 is a simplified restriction map of a portion of B. licheniformis DNA in a B. subtilis plasmid.

FIG. 3 is the nucleotide and amino acid sequence of the 5' terminus of the B. licheniformis α-amylase gene.

FIG. 4 is a comparison of the amino acid sequences of the α-amylase genes of B. licheniformis and B. amyloliquefaciens.

FIG. 8 is the nucleotide and amino acid sequence of the area of fusion of the B. licheniformis α-amylase signal encoding sequence and the alkaline phosphatase gene in pNH218.

FIG. 10 is the nucleotide and amino acid sequence of the area of fusion of the B. licheniformis α-amylase signal encoding sequence and the alkaline phosphatase gene in p2/38.

FIG. 15 is a diagrammatic representation of a plasmid containing a gene encoding APIII.

FIGS. 31 (a and b) are diagrammatic representations of the synthetic GRF gene and linker sequence.

Figure 1:
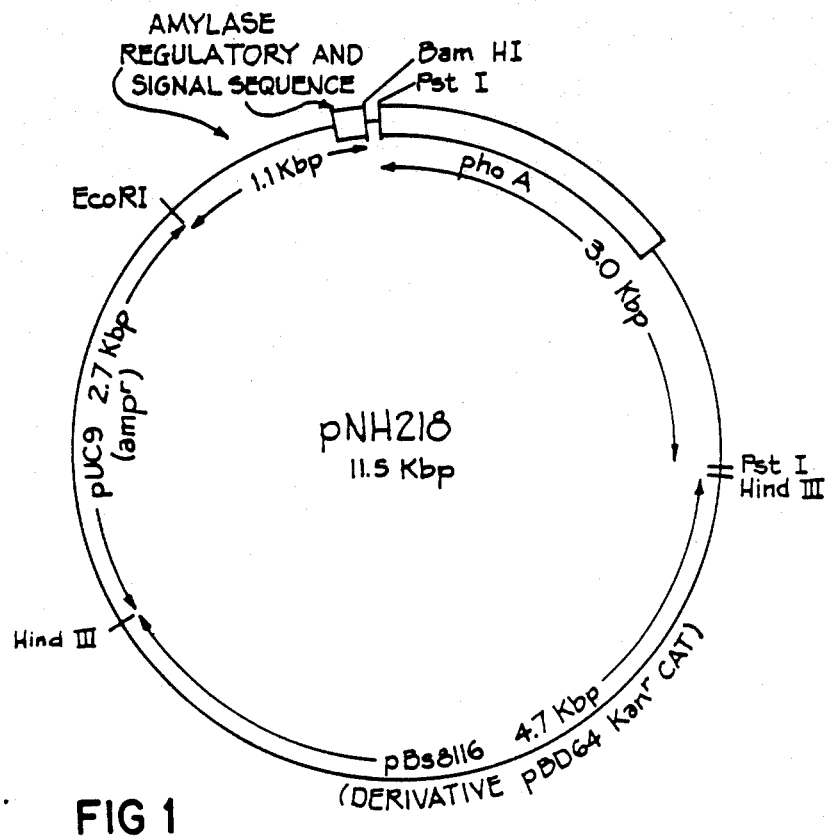
FIG. 1 is a diagrammatic representation of a vector, pNH218, of the invention.

FIGS. 2, 3, and 4 are taken from Stephens, Ortlepp, Ollington, and McConnell (1984) J. Bacteriol. 158, 369-372.

Vector Components

As is mentioned above, a vector of the invention useful for the transformation of host bacterial cells for the production and secretion of a desired heterologous polypeptide includes several components, now discussed in more detail.

Promoter and Ribosome Binding Site Sequences

Any promoter and ribosome binding site sequences which function in Gram positive bacteria such as Bacillus species can be employed. Preferably, these sequences are substantially identical to naturally occurring Bacillus sequences, e.g., sequences of B. subtilis, B. licheniformis, B. amyloliquefaciens, or B. thuringiensis. Sequences derived from other Gram positive species, e.g., Staphylococci and Streptococci species, can also be employed. The promoter and ribosome binding site sequences must be upstream of the DNA encoding the in-frame signal and heterologous protein-encoding sequences, and are preferably at a distance from the translational start site of the signal-encoding sequence which effects optimal expression. Suitable naturally occurring Bacillus promoter and ribosome binding site sequences are those functionally associated with Bacillus genes encoding enzymes, e.g., α-amylase, and with genes involved in sporulation, e.g., the spoVG gene from Bacillus species. The choice of the promoter will depend on the application; in some instances, a strong constitutive promoter will be desirable, and in others, a regulated promoter (such as some of the sporulation promoters) will be used. As will be described in greater detail below, promoterless vectors in which a structural gene, e.g., a gene encoding an enzyme such as α-amylase, is preceded not by its own promoter but by a restriction site, can be used to screen DNA fragments for promoter activity.

B. licheniformis Secretory Signal Sequence

The DNA encoding this sequence is preferably isolated from the B. licheniformis α-amylase gene, as described in more detail below. Alternatively, the DNA encoding the sequence can be produced synthetically using conventional DNA synthesis techniques. In addition, the DNA sequence (whether natural or synthetic) can be modified in any way which does not substantially impair the ability of the encoded signal sequence to effect secretion of the heterologous polypeptide.

Heterologous DNA Sequence and Site

The site for insertion of the heterologous DNA sequence is downstream from the 3' end of the DNA encoding the signal sequence, preferably directly adjacent to the 3' end or within a few codons of it, so that the heterologous polypeptide portion of the resulting hybrid protein is carried out of the cell by the signal sequence, and so that few or no extraneous amino acids will remain after cleavage of that sequence. Insertion of the heterologous DNA sequence is facilitated if the restriction site is unique in the vector. The site can be naturally occurring in the vector, or it can be synthetically added. A translation termination sequence can be added downstream from the heterologous gene, to ensure that the protein carried out of the cell by the signal sequence does not include the α-amylase enzyme.

An alternative method of constructing a vector in which a gene for a heterologous polypeptide is located downstream from the B. licheniformis α-amylase signal encoding sequence is to insert the heterologous gene into a vector containing the entire α-amylase gene, between the signal-encoding sequence and the structural gene, at the C-terminus of the structural gene, or within the structural gene; this can be done using an existing or synthetically added restriction site. It can be advantageous in some instances (particularly in the case of small peptides and polypeptides) to introduce the heterologous gene into the vector in such a way as to produce a hybrid polypeptide, composed of all or a portion of the α-amylase enzyme fused to the polypeptide encoded by the heterologous gene. The hybrid is more resistant to proteolysis than the desired polypeptide alone, and yield is thus increased. Following recovery of the hybrid polypeptide, the α-amylase portion is removed, using conventional techniques.

The heterologous DNA can encode any desired polypeptide, e.g., medically useful proteins such as hormones, vaccines, antiviral proteins, antitumor proteins, antibodies, or blood clotting proteins, and agriculturally and industrially useful proteins such as enzymes or pesticides. Useful heterologous polypeptides which, like alkaline phosphatase, have been produced and secreted according to the invention, are GRF and APIII.

A particular vector of the invention, pNH218, is illustrated in FIG. 1, and its structure and construction described below.

Structure of pNH218

FIG. 1 is a diagrammatic representation of pNH218, a vector in which the heterologous E. coli gene for the enzyme alkaline phosphatase is inserted adjacent the DNA encoding the B. licheniformis α-amylase signal sequence, under the transcriptional and translational control of the B. licheniformis promoter and ribosome binding sequences.

Construction

The first step in the construction of pNH218 was the isolation of the B. licheniformis signal sequence, which was carried out as follows.

Isolation of Signal Sequence

The α-amylase gene of B. licheniformis strain FD02, cloned into a B. subtilis replicon by Ortlepp et al. and described in Gene (1983) 23, 267, was obtained and localized to a 3.5 kb EcoRI fragment of DNA on the recombinant plasmid pSA33. A simplified restriction endonuclease map of the B. licheniformis DNA is shown in FIG. 2, in which the numbers indicate distances in kilobases (kb), and the thick horizontal line shows the location of the α-amylase gene.

The 1.1kb EcoRI—PstI fragment and the 2.3 kb PstI fragment were subcloned from pSA33 into the E. coli plasmid pUC8, described in Vieira et al. (1983) Gene 19, 259. This was achieved by cleaving pSA33 with EcoRI and PstI and ligating the resulting fragments to pUC8 cut with PstI or double cut with EcoRI and PstI. The ligation mixture was transformed into E. coli strain JM83, and colonies containing plasmid DNA selected by plating the transformed cells onto agar plates containing ampicillin (30 μg/ml) and the chromogenic dye 5-bromo-4-chloro-3-indolyl-β-D-galactoside (X gal) using standard techniques. The cells containing recombinant plasmids were screened for the presence of inserts using the plasmid isolation procedure of Birnboim et al. (1979) Nucl. Acids Res. 7, 1513-1522.

Plasmid pEc20/7 was found to contain the 1.1kb EcoRI-PstI fragment (fragment A in FIG. 2) of pSA33, while plasmid pEc20/9 was found to contain the 2.3kb PstI fragment of pSA33 (fragment B of FIG. 2).

The DNA in pEc20/7 and pEc20/9 was sequenced on both strands from the HindIII site of the pUC8 moiety, across the PstI site, into the *B. licheniformis* DNA, using standard DNA sequencing techniques. To the right of the PstI site in pEc20/9 an open reading frame was detected that would encode an amino acid sequence almost identical to the first 18 amino acids of the mature *B. licheniformis* α-amylase protein reported by Kuhn et al. (1982), J. Bacteriol. 149, 372. It was concluded, therefore, that the coding region of the mature α-amylase protein was on pEc20/9.

Examination of the DNA upstream from the coding region indicated that the mature protein is preceded by an open reading frame encoding a 29 amino acid chain which commences with a methionine residue. The amino acid composition of this sequence is consistent with that of a signal sequence: a positively charged $NH_2$-terminus is followed by an extensive hydrophobic region preceding the coding sequence for the mature protein. This signal sequence is considerably longer and more positively charged at the $NH_2$-terminus than reported signal sequences from Gram negative bacteria such as *E. coli*, but is characteristic of a signal sequence from a Gram positive organism. The translation initiation codon of the signal sequence-encoding DNA is preceded by a strong ribosome binding site (Shrine-Dalgarno sequence), and a sequence for the initiation of transcription of the gene, i.e., the promoter sequence.

The *B. licheniformis* α-amylase promoter and ribosome binding site and most of the DNA encoding the signal sequence were found to be located on pEc20/7.

Nucleotide Sequence of Signal Encoding DNA

Referring now to FIG. 3, there is shown the nucleotide and deduced amino acid sequence of the 5' terminus of the *B. licheniformis* α-amylase gene (the nontranscribed strand of the DNA is shown). The ribosome binding site is underlined, and the predicted cleavage site between the signal and mature sequences is indicated with a vertical bar. The consensus sequences for promoters recognized by the principal form of RNA polymerase in exponentially growing *B. subtilis* cells are TTGACA and TATAAT in the −35 and −10 regions, respectively; these are shown in FIG. 3, above the putative promoter for the α-amylase gene. The comparable sequences just upstream of the *B. licheniformis* α-amylase gene are TTGTTA and TACAAT, respectively.

Referring now to FIG. 4, there is shown a comparison between the deduced amino acid sequences of the products of the α-amylase genes of *B. licheniformis* (B.l.) and *B. amyloliquefaciens* (B.a.) (Palva et al. (1981) Gene 15, 43–51). Homology is denoted with an asterisk. The predicted cleavage site between the signal sequence and the mature sequence is indicated with a vertical bar.

As shown in FIG. 4, although the proteins exhibit a high degree of homology in the first 75 amino acids of the mature proteins, there are only a few short regions of homology between the two signal sequences.

Role of Signal Sequence in Secretion

The importance of the signal sequence in the secretion of *B. licheniformis* α-amylase was demonstrated by showing that while removal of DNA upstream of the ribosome binding site and signal sequence encoding region reduced secretion significantly, removal of most of the DNA encoding the signal sequence eliminated secretion completely.

Storage Vector for the Signal

Figure 5:
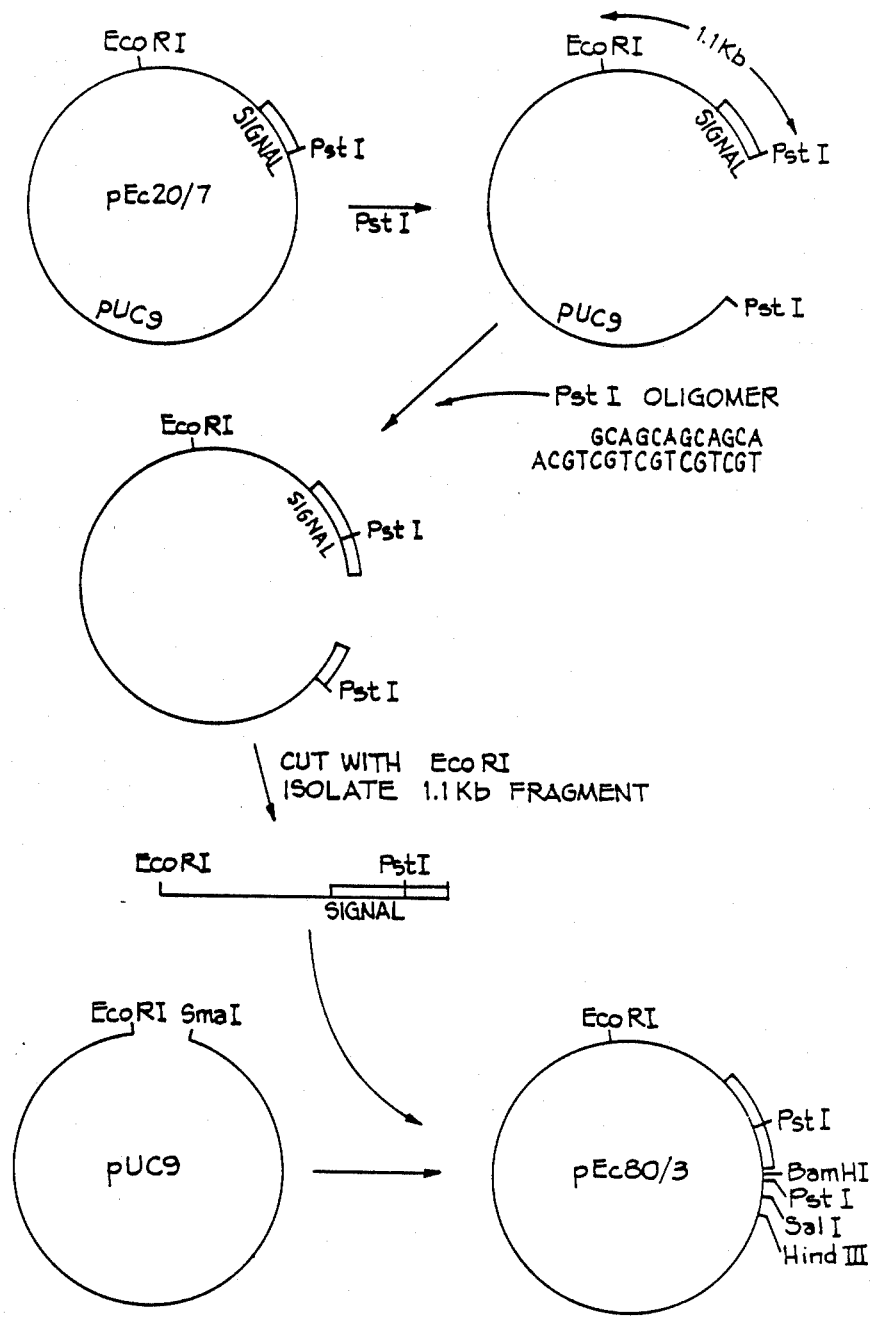
FIG. 5 is a diagrammatic representation of the construction of an intermediate vector containing the B. licheniformis α-amylase signal encoding sequence.

Referring to FIG. 5, the signal encoding DNA of pEc20/7 was attached to a linker and inserted into pUC9 to form signal DNA-encoding storage vector pEc80/3, as follows.

The 1.1 kb EcoRI-PstI fragment on pEc20/7 contains most, but not all, of the DNA encoding the *B. licheniformis* α-amylase signal sequence; the DNA encoding the last three amino acid residues are missing. In order to obtain a DNA sequence coding for a complete signal sequence, a sequence of synthetic DNA was attached to the PstI site of pEc20/7, thus reconstituting the DNA sequence coding for a complete signal sequence.

In more detail (FIG. 5) pEc20/7 was cleaved with PstI and the illustrated DNA oligomer, synthesized by standard chemical methods, was ligated to the exposed PstI ends. The ligation mixture was then cleaved with EcoRI and the resulting 1.1 kb fragment was isolated, ligated between the EcoRI and SmaI sites of the *E. coli* plasmid pUC9, and transformed into *E. coli* strain JM83. One of the resulting plasmids, pEc80/3, was shown by DNA sequence analysis to contain a DNA sequence coding for a complete signal sequence.

Storage Vector for the Alkaline Phosphatase Gene

The *E. coli* phoA gene encoding alkaline phosphatase, that had been Bal31 digested to remove the signal sequence and the first five to thirteen amino acids of extracellular alkaline phosphatase, was cloned, in each of three reading frames in both possible orientations, in the PstI site of pUC8. One of the resulting plasmids was pNH214, shown in FIG. 6. (The Bal31-digested cloned phoA gene was obtained from A. Wright, Department of Microbiology and Molecular Biology, Tufts University School of Medicine, Boston, Mass., or it can be obtained as described in Inouye et al., (1981) J. Bacteriol. 146: 668–675.)

Construction of pNH216

Figure 6:
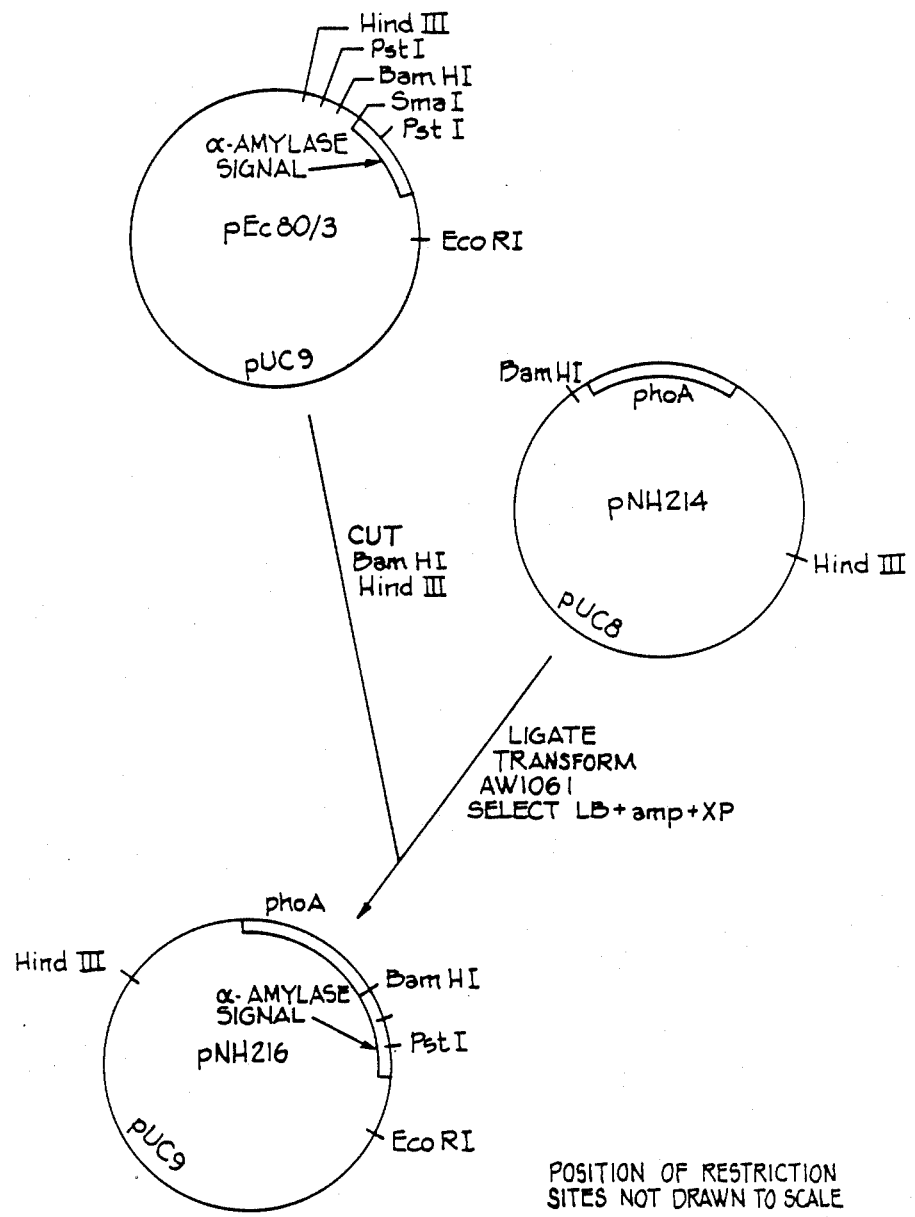
FIG. 6 is a diagrammatic representation of the construction of an E. coli vector containing the B. licheniformis α-amylase signal encoding sequence and the alkaline phosphatase gene.

Referring still to FIG. 6, pNH214 was cut with BamHI and HindIII, so that the entire phoA coding region was contained on a ≈3 kb fragment. This DNA was mixed with DNA from pEc80/3 (containing the complete α-amylase signal sequence) previously cut with BamHI and HindIII. After ligation of this mixture, the resulting DNA was transformed into *E. coli* AW1061, and the cells grown on LB plates in the presence of ampicillin and 5-bromo-4-chloro-3-indolyl phosphate ("X-P"). Colonies expressing alkaline phosphatase were identified by a plate assay in which X-P turns blue upon cleavage by the enzyme. One of these colonies carried the plasmid pNH216, which encoded the entire signal sequence of amylase followed by a glycine, six additional amino acids created by linker DNA, and alkaline phosphatase beginning at amino acid 5. pNH216 is an *E. coli* vector capable of replication and production of alkaline phosphatase in *E. coli* and other Gram-negative bacteria; it is not capable of replication in Bacillus. The secretion of alkaline phosphatase by *E. coli* containing pNH216 demonstrates that this signal sequence function in *E. coli*.

Construction of pNH218

Figure 7:
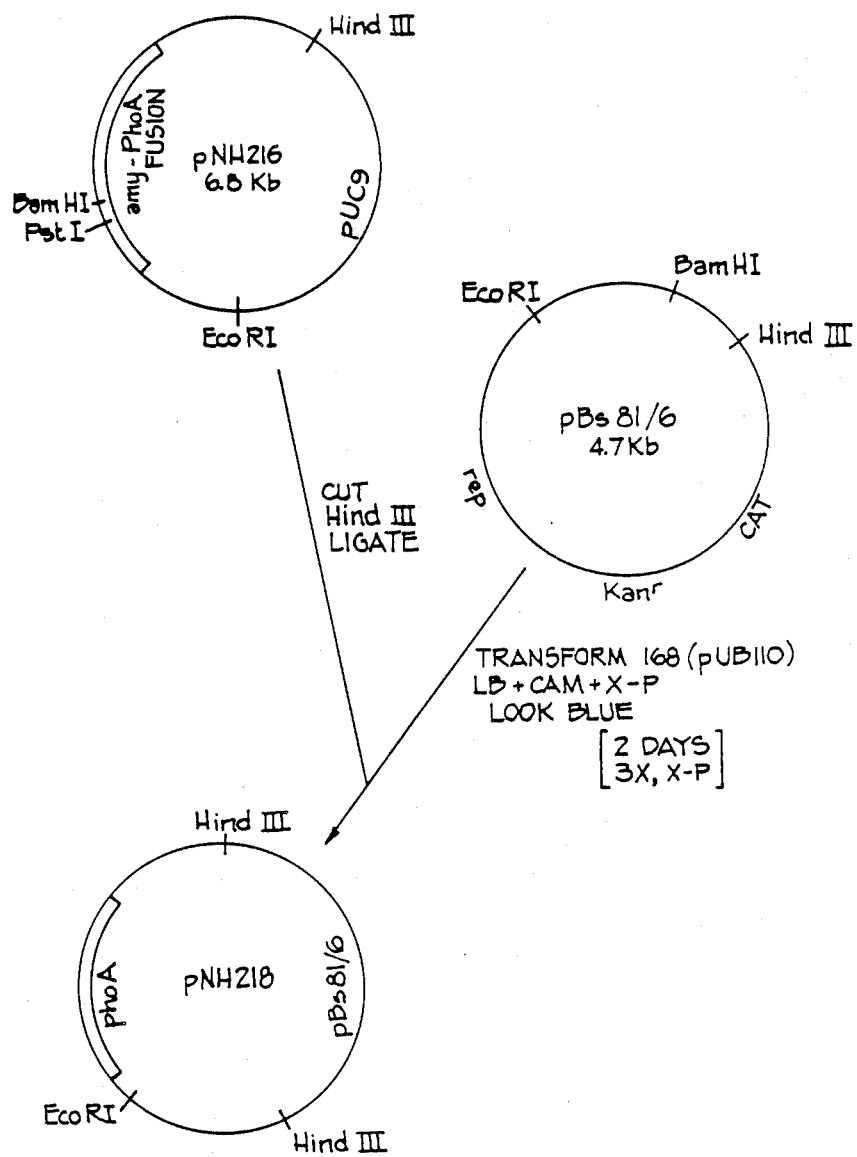
FIG. 7 is a diagrammatic representation of the construction of pNH218.

Referring now to FIG. 7, the next stage was to enable replication of the sequences of interest in Bacillus. pNH216 was cut at its HindIII site and ligated to the Bacillus plasmid pBs81/6, which had also been linearized at its HindIII site. The resulting DNA was transformed into *B. subtilis* strain 168(pUB110), which was grown on LB plates with 5 µg/ml chloramphenicol and X-P. Transformants identified by the X-P plates assay carried plasmid pNH218, in which the fusion of the *B. licheniformis* α-amylase signal encoding sequence and the phoA gene are carried on a vector able to replicate in Bacillus. pNH218 was maintained in *B. subtilus* strain 168.

Secretion of Alkaline Phosphatase

Secretion of functional alkaline phosphatase was detected by the appearance of blue colonies on the plate assay, indicating expression of the phoA gene in *B. subtilis*. The convenient plate assay for alkaline phosphatase renders pNH218 (or other alkaline phosphatase-encoding vectors such as p2/38 and pCR25) useful in screening vector constructions, promoters, ribosome binding sites, vector mutations, or host strains and host mutations for those that maximize protein expression and secretion. Such screening can be carried out using the phoA gene by itself, or the phoA gene fused to all or a portion of a gene encoding a desired heterologous polypeptide. The testing method involves producing a vector including a promoter, a ribosome binding site, and a secretory signal-encoding sequence of a Bacillus gene, and, downstream from and in frame with the signal-encoding sequence, a DNA sequence encoding alkaline phosphatase or an enzymatically active portion thereof; transforming host Gram positive cells with the vector; and culturing the transformed cells on a medium including an indicator substance capable of undergoing a detectable change in the presence of alkaline phosphatase. The testing method can employ either liquid media or plates with indicator substance. Degree of detectable change is related to efficiency of expression and secretion.

In exemplary test culture conditions, host Gram positive cells, transformed with the fused DNA, are assayed on plates containing X-P, or are grown under appropriate conditions, e.g., at 37° C., with aeration, in nutrient LB broth containing, per liter, 10 g Difco Bacto tryptone, 5 g Difco yeast extract, and 5 g NaCl. Culture samples are taken at various times, centrifuged, and supernatant fractions assayed for product, e.g., by the yellow color-based assay described in Brickman et al. (1975) J. Mol. Biol. 96, 1–10. Maximum accumulation of the product occurs after 1-2 days.

pNH218 can also be used to effect the expression in *B. subtilis* of any desired heterologous gene, by removing the alkaline phosphatase gene and replacing it with the desired gene, in-frame with the signal encoding sequence, using conventional techniques.

Figure 9:
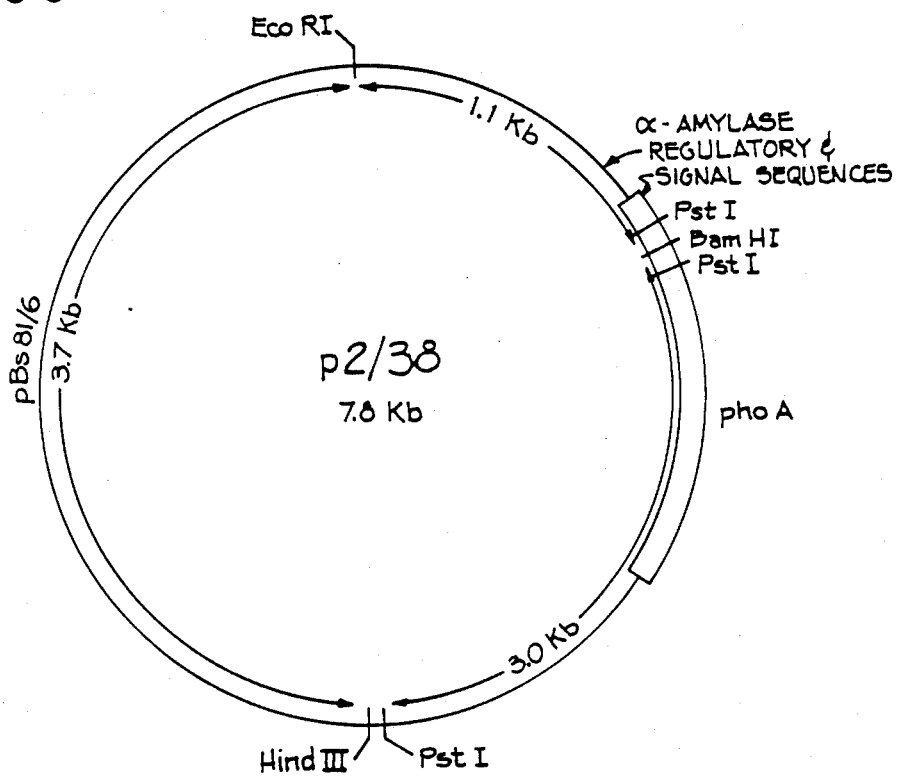
FIG. 9 is a diagrammatic representation of a vector, p2/38, of the invention.

A second vector of the invention, p2/38, is illustrated in FIG. 9, and its structure and construction described below.

Structure and Construction of p2/38

FIG. 9 is a diagrammatic representation of p2/38, a vector which contains the *B. licheniformis*-derived components of pNH218 but which, unlike pNH218, is only a *B. subtilis* vector and does not contain an *E. coli* replicon. Also, the area of fusion of the DNA encoding the α-amylase signal and alkaline phosphatase differ, in sequence and reading frame. This area is illustrated for pNH218 in FIG. 8 and for p2/38 in FIG. 10.

p2/38 was constructed using DNA fragments similar to those used to construct pNH218. The signal-encoding DNA of pEc20/7 was attached by standard methods to a synthetic PstI to BamHI linker whose sequence is shown in FIG. 10. The signal-encoding DNA plus linker was cloned into pUC9 for storage (p218/4). A BamHi-HindIII fragment containing the phoA gene was isolated from pNH221 (a pUC9 plasmid analogous to pNH214, but with the phoA gene in a different reading frame) and cloned between the BamHI and HindIII sites of the Bacillus plasmid pBs81/6 to yield plasmid p40/15. Finally, an EcoRI to BamHI fragment containing the signal-encoding DNA plus linker from p218/4 was cloned between the EcoRI and BamHI sites of p40/15 to yield the plasmid p2/38.

Figure 13:
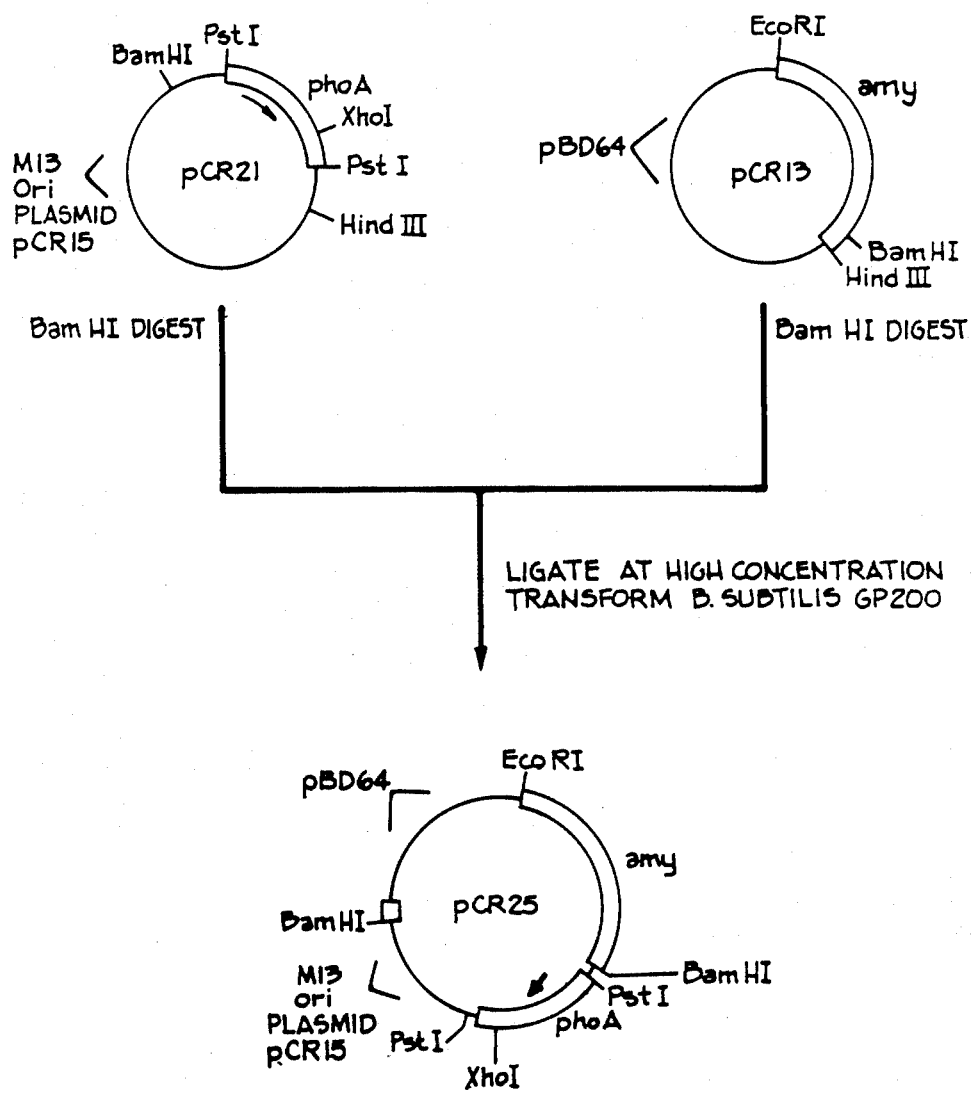
FIGS. 13 and 14 are diagrammatic representations of the construction of a plasmid containing the B. licheniformis α-amylase gene and the E. coli phoA gene.

A third vector of the invention, pCR25, is illustrated in FIG. 13, and its structure and construction from an intermediate plasmid, pCR13, described below.

Structure and Construction of pCR13

Figure 11:
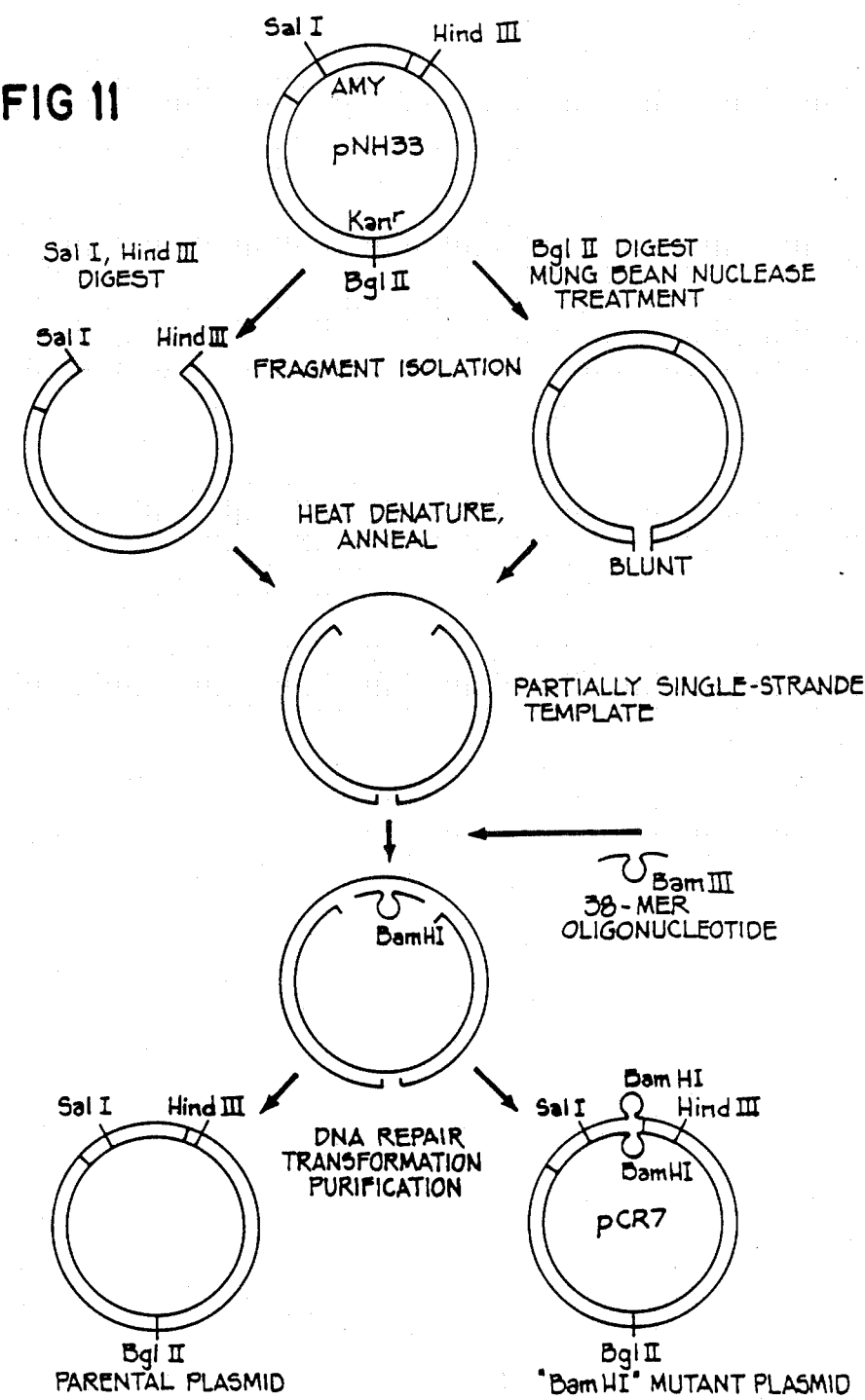
FIGS. 11 and 12 are diagrammatic representations of the construction of a plasmid containing the B. licheniformis α-amylase gene and a unique BamHI site.
Figure 12:
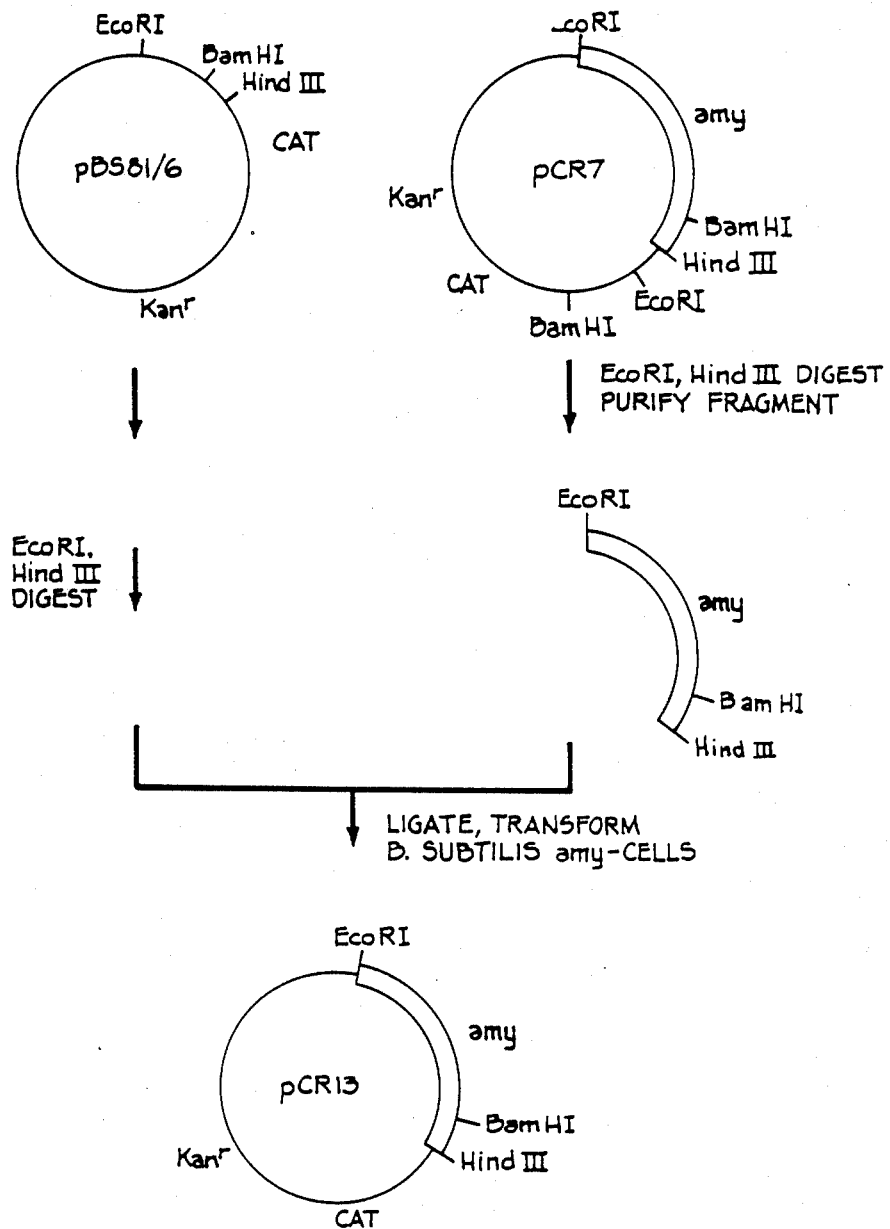

FIGS. 11 and 12 are diagrammatic representations of the construction of pCR13, a vector which contains the *B. licheniformis* α-amylase gene with a unique BamHI restriction enzyme site at its 3' end, so that any desired gene can be readily fused to the carboxy-terminus of the α-amylase gene; one such gene, the *E. coli* alkaline phosphatase gene, was inserted into pCR13 to produce pCR25, as described below.

Referring to FIG. 11, pCR13 was constructed as follows. Oligonucleotide-directed mutagenesis was performed using a 38-residue synthetic oligonucleotide sequence which is complementary to the nucleotide sequence on either side of the *B. licheniformis* α-amylase stop codon, and which contains an additional six base pairs encoding a BamHI restriction site. These additional base pairs, coding for the amino acid glycine and serine, are introduced between the last codon and the stop codon.

Still referring to FIG. 11, the 38-mer oligonucleotide was annealed to a partially single-stranded template prepared from pNH33 (derived from pSA33, above), containing the *B. licheniformis* α-amylase gene, including regulatory elements and the secretory signal encoding sequence, and also containing genes for kanamycin and chloramphenicol resistance. This template was obtained by annealing a mixture of fragments of pNH33 derived by restriction digestion with SalI and HindIII or with BglII followed by Mung bean nuclease treatment. One fragment contained an intact α-amylase gene but lacked a functional kanamycin resistance gene, while the other fragment was deleted for the region of DNA that includes the 3' termius of the α-amylase gene. The annealed complex of oligonucleotide and template was treated with DNA polymerase to incorporate the oligonucleotide into the newly repaired strand. The mutagenized DNA was used to transform *B. subtilis* protoplasts and transformants were selected by chloramphenicol resistance and screened for kanamycin resistance and the ability to make α-amylase. Plasmids from these transformants were screened for the new BamHI site. One of these plasmids, pCR7 (FIG. 12), was isolated and shown to have a BamHI site at the carboxy-terminal end of the α-amylase gene.

The parental plasmid of pCR7, pNH33, has an additional BamHI site in the vector backbone. To construct a plasmid in which the newly created BamHI site was unique, the EcoRI-HindIII fragment of pCR7, containing the α-amylase gene with the new 3' BamHI site, was cloned into EcoRI, HindIII-treated pBs81/6 to form pCR13 (FIG. 12).

Amylase activity of the pCR13-encoded α-amylase, which contained an additional glycine-serine at its carboxy-terminal end, was determined by a starch-azure plate assay, carried out as follows. Petri dishes containing a bottom layer of nutrient agar and a top layer of nutrient agar containing blue-colored starch azure as an indicator were prepared by first pouring nutrient agar (1.5% agar) into each dish, allowing that layer to solidify, and then pouring, on top of the first layer, a top layer (⅓ the volume of the petri dish) containing nutrient agar (1.5% agar) and 0.5% (w/v) starch azure (Sigma Cat. No. 57629) and allowing the top layer to solidify. After drying to remove excess moisture, cells were spread or streaked onto the plates and incubated for 12-24 hours. Colonies containing cells secreting amylase were detected by the appearance of clear halos on a background of blue colored starch azure in the top layer. This two-layer system was found to provide greater sensitivity than systems in which the starch azure is distributed throughout all of the nutrient agar on the plate.

The addition of glycine-serine to the carboxy-terminal end of the pCR13-encoded α-amylase did not appear to affect amylase activity, as judged by the size of halos on the starch azure medium described above, although the presence of additional amino acids at the carboxy-terminal end of α-amylase often does result in some reduction of halo size. Thus measurement of halo size of transformants on starch azure agar plates can be used, as it was for the alkaline phosphatase gene in pCR25, below, as a preliminary screen for inserts at the BamHI site of pCR13.

Figure 14:
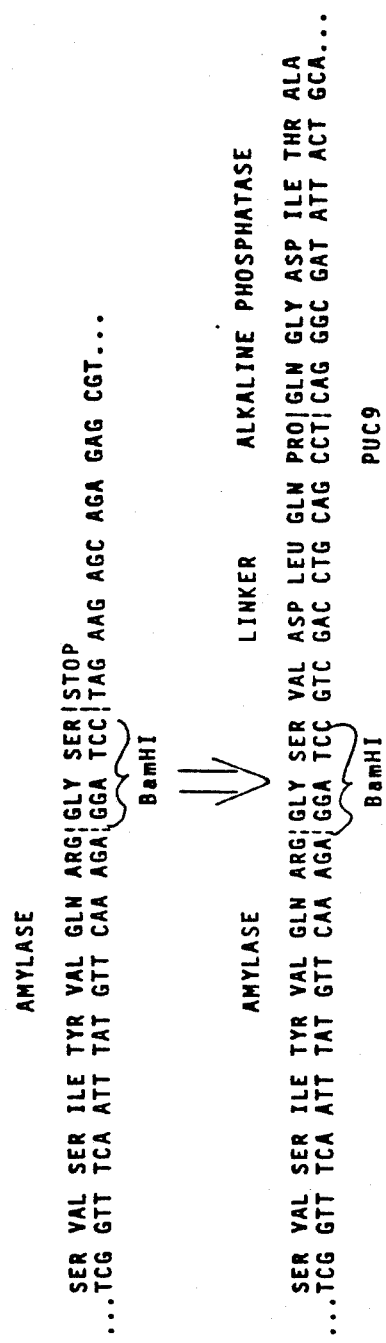

To construct pCR25, the $E.\ coli$ alkaline phosphatase gene was introduced into the newly created BamHI site in the α-amylase gene in pCR13 as follows. Referring to FIG. 13, to effect the correct fusion of the α-amylase gene to the alkaline phosphatase gene, plasmid pCR21, with a unique BamHI site upstream from the phoA gene in the correct frame with respect to the α-amylase and the phoA sequences (FIG. 14) was cut with BamHI, and the BamHI fragment inserted at the BamHI site of pCR13.

The ligated DNA, above, was used to transform $B.\ subtilis$ strain GP200 (a protease-deficient strain carrying mutations in both the subtilisin and neutral protease genes). Transformants were selected on the basis of chloramphenicol resistance, and then further selected for amylase and alkaline phosphatase activity using the two-layer plates described above. Of 59 transformants screened, 42% has reduced halo diameters on starch azure plates. Approximately half of those transformants that displayed reduced halo sizes also made alkaline phosphatase, as measured by blue halos on X-P plates. No transformants were found that displayed alkaline phosphatase activity without concomitant starch azure halo reductions. One transformant that had a reduced halo size and made alkaline phosphatase contained plasmid pCR25.

Secretion of Alkaline Phosphatase

The culture supernatants of bacteria carrying pCR25 were assayed for alkaline phosphatase antigen by Westen blotting. The amylase-alkaline phosphatase fusion protein was detected in the culture supernatant of the strain carrying pCR25 as a full length protein of approximately 100kd. This demonstrated that a carboxy-terminal α-amylase fusion can effect secretion of a heterologous protein.

Figure 16:
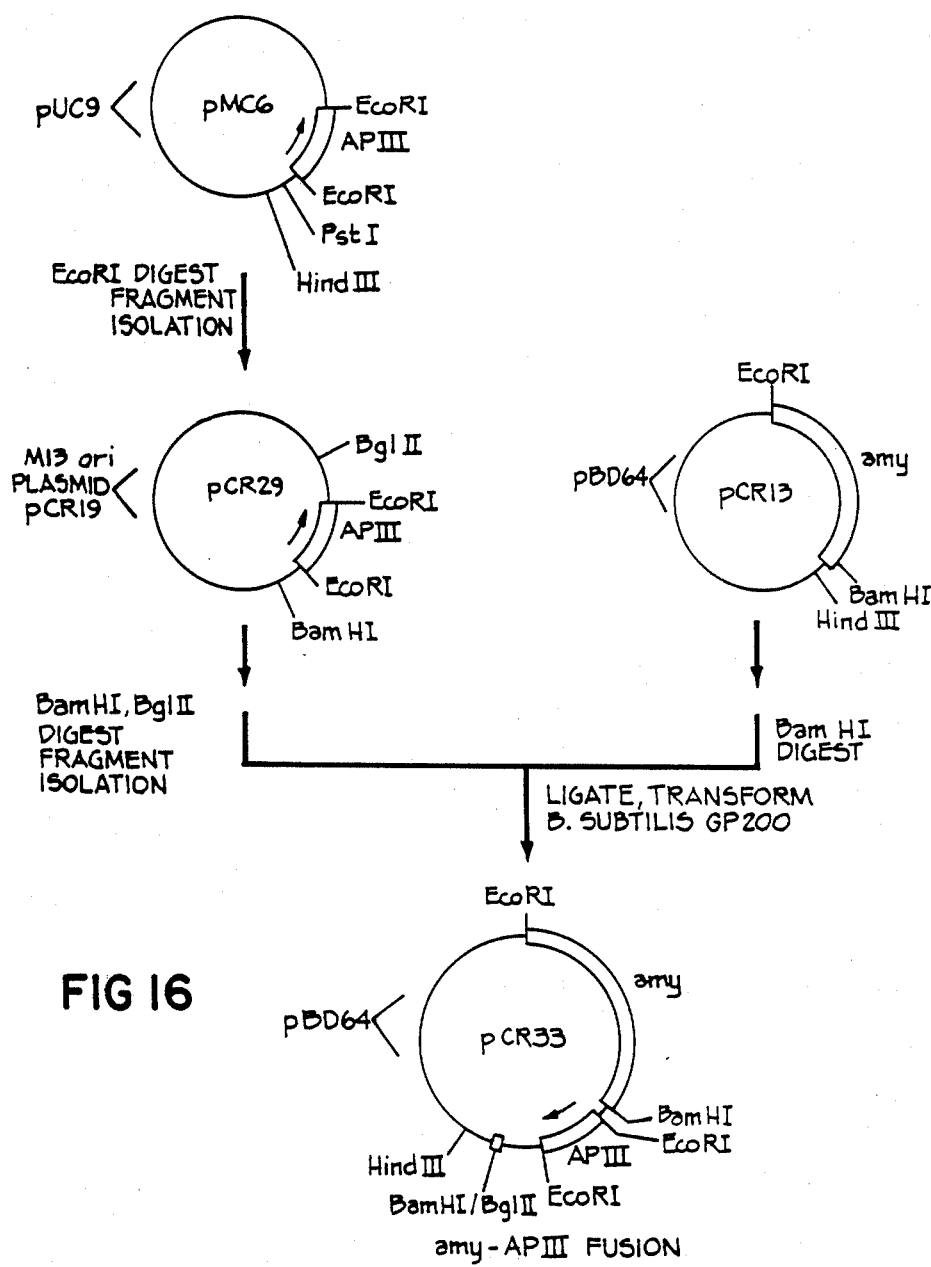
FIGS. 16–18 are diagrammatic representations of the construction of α-amylase-APIII fusions.
Figure 17:
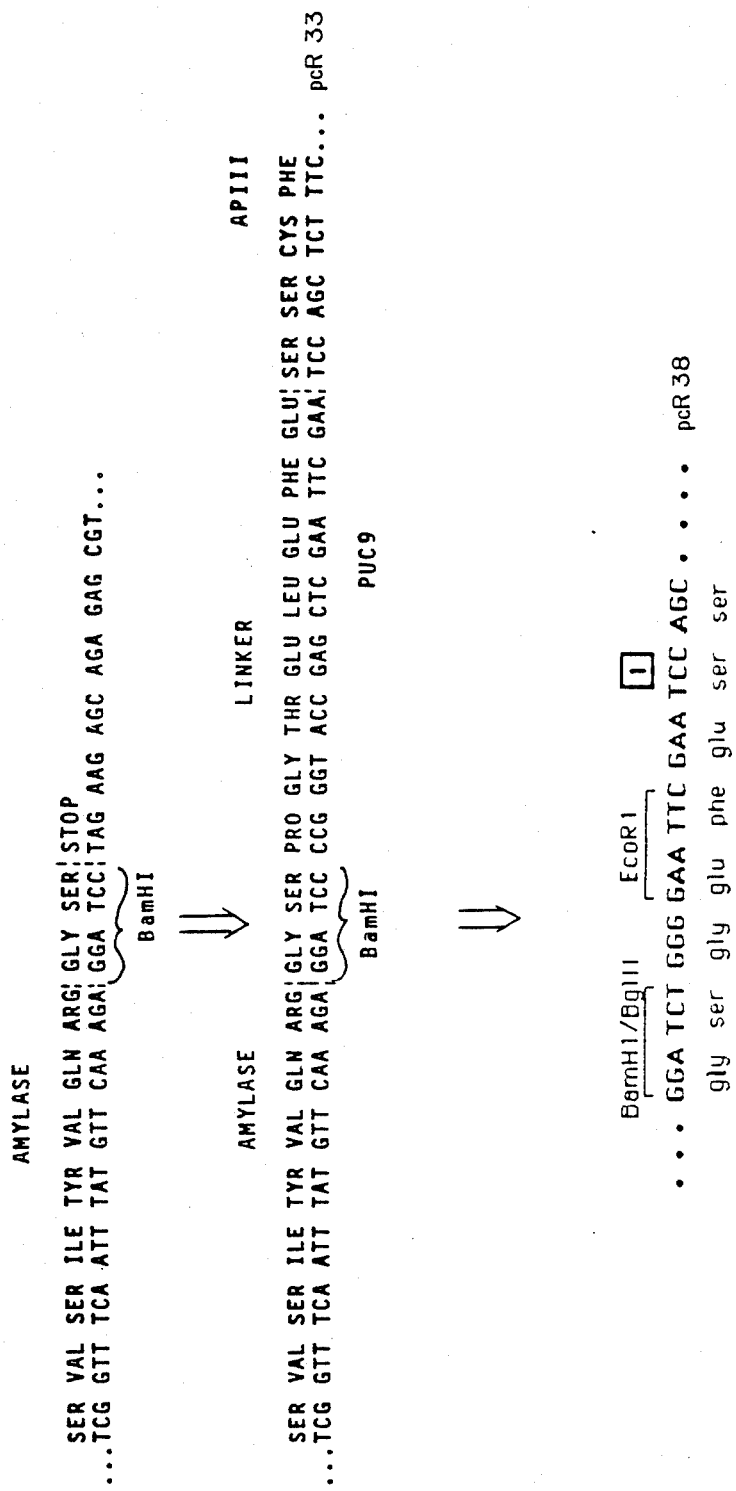

Additional vectors of the invention, pCR33 and pCR38, are illustrated in FIGS. 16 and 17, and their structure and construction described below.

Structure and construction of pCR33 and pCR38 mMC6 (FIG. 15(a)) contains the entirety of a synthetic gene encoding APIII on an EcoRI fragment of 93 base pairs. The base pair and amino acid sequences are given in FIG. 15(b).

The correct fusion of the APIII gene to the α-amylase gene required the addition of a BamHI site in the proper reading frame to the 5' end of the APIII gene.

To achieve this, the EcoRI fragment of pMC6 containing the APIII gene was cloned into pCR19 (FIG. 16). The cloning of the APIII gene in the desired orientation in pCR19 produced plasmid pCR29 (FIG. 16), in which the unique BamHI site of the polylinker was in the correct frame with respect to α-amylase and APIII sequences. The unique BglII site in pCR29 permitted the isolation of the APIII gene on a BamHI-BglII DNA fragment.

Referring to FIGS. 16 and 17, the BamHI-BglII APIII gene fragment from pCR29 was inserted into the BamHI site of pCR13 and the ligated DNA used to transform the protease-deficient $B.\ subtilis$ strain GP200. When scored for α-amylase production on starch agar plates, about 20% of the chloramphenicol resistant transformants had reduced halos. The plasmid of one selected transformant was confirmed as having the desired orientation of the BamHI-BglII APIII fragment in pCR13.

Figure 18:
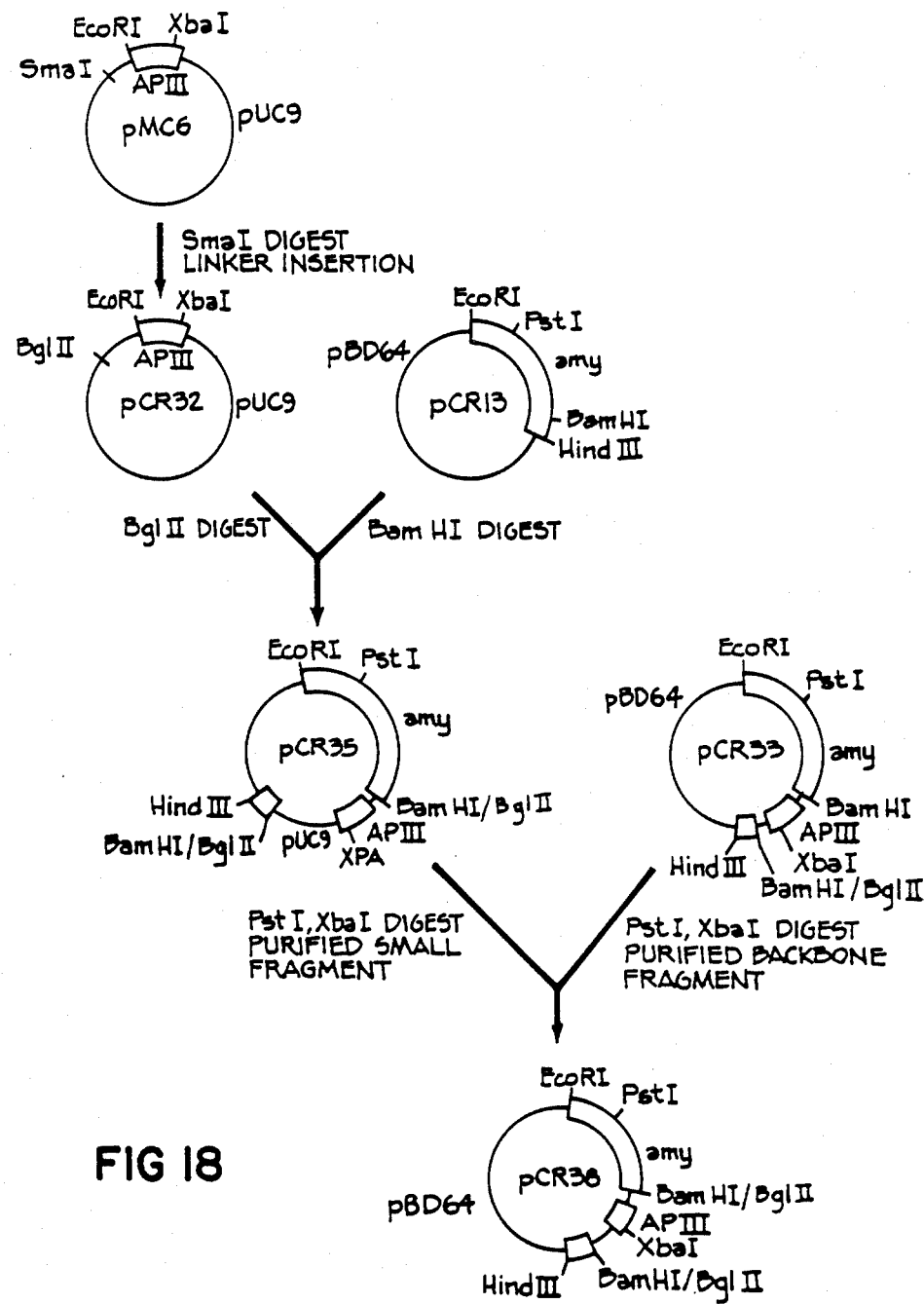

FIG. 17 illustrates the construction of pCR33 by the insertion of APIII/linker DNA into the BamHI site of pCR13, and gives the predicted sequence around the fusion. FIG. 17 also illustrates an additional plasmid, pCR38, containing α-amylase and APIII encoding genes; pCR38 has a predicted 18 base pair sequence between the end of the α-amylase encoding gene and the beginning of the APII encoding gene, compared to 30 base pairs in pCR33. Referring to FIGS. 17 and 18, plasmid pCR38 was constructed as follows. Plasmid pMC6 was cut with SmaI in the linker region 5' to the APIII sequence. A commercial DNA linker was inserted at the SmaI site to create a BglII site. After cleavage with BglII, the resulting plasmid was cloned into the BamHI site of pCR13 to create an amylase-APIII fusion contained on a bifunctional replicon. The PstI—XbaI fragment containing the amylase-APIII fusion was then cloned into the PstI—XbaI backbone of pCR33. The final construction, pCR38, is identical to pCR33 except in the linker sequences between the amylase and APIII genes.

Secretion of amylase-APIII

The fusion proteins produced in vivo were examined by growing isolates of $B.\ subtilis$ strain GP200 carrying the plasmids pCR33 or pCR38 for a five minute period in minimal medium containing radioactively labelled methionine. The "pulse" of incorporation of labelled methionine was terminated by the addition of sodium azide and an excess of unlabelled methionine, and the supernatant and cell fractions were probed for α-amylase and APIII antigen by immunoprecipitation. The precipitated material was fractionated by gel electrophoresis and visualized by autoradiography.

The strains carrying pCR33 or pCR38 synthesized a polypeptide specifically immunoprecipitable with rabbit anti-α-amylase. This polypeptide, which was approximately 4000 daltons larger than the α-amylase of pCR13, was found in both the supernatants and cell fractions, and was not seen in pCR13 or pBD64 controls. There also appeared to be minor bands in the pCR33 and pCR38 samples that were roughly the same molecular weight as the pCR13 α-amylase.

The polypeptides specifically precipitated by rabbit anti-α-amylase were secondarily precipitated by rabbit anti-atriopeptin antiserum. Two polypeptides in the pCR33 and pCR38 supernatant samples were immunoprecipitable with α-amylase antisera. The upper band, representing a polypeptide approximately 3-4 kd larger than the amylase of pCR13, was also precipitable by rabbit anti-atriopeptin. The lower band, present in lesser amount than the upper band, was not recovered in the APIII immunoprecipitates. The upper band of the pCR33 and pCR38 samples represents the α-amylase-APIII fusion protein, by the criteria of molecular weight and antigenicity. The second polypeptide, similar in size to the α-amylase of pCR13, may represent fusion protein not containing APIII.

The proteins accumulated in cultures of GP200 carrying pCR33 were examined for α-amylase and APIII antigenicity using Western blotting. Cultures were grown in Penassay broth plus 5 μg/ml chloramphenicol and samples of supernatants and cells were taken 2.5 and 19.5 hrs into stationary phase. APIII and α-amylase antigenicity were detected at both timepoints in the supernatant and cell fractions of the strain containing pCR33. The single band detected in the pCR33 supernatants and cell fractions with rabbit anti-atriopeptin antisera appeared to have the same mobility as the protein band recovered by immunoprecipitation of pulse-labeled cells using rabbit anti-atriopeptin.

Polyacrylamide gel analysis and in situ α-amylase assays of the 19.5 hr timepoint supernatant samples of GP200 carrying pCR33 confirmed that the strain secreted a polypeptide that the α-amylase activity and was larger than the α-amylase of pCR13. This protein band is not seen in the pCR13 or pBD64 controls.

Figure 20:
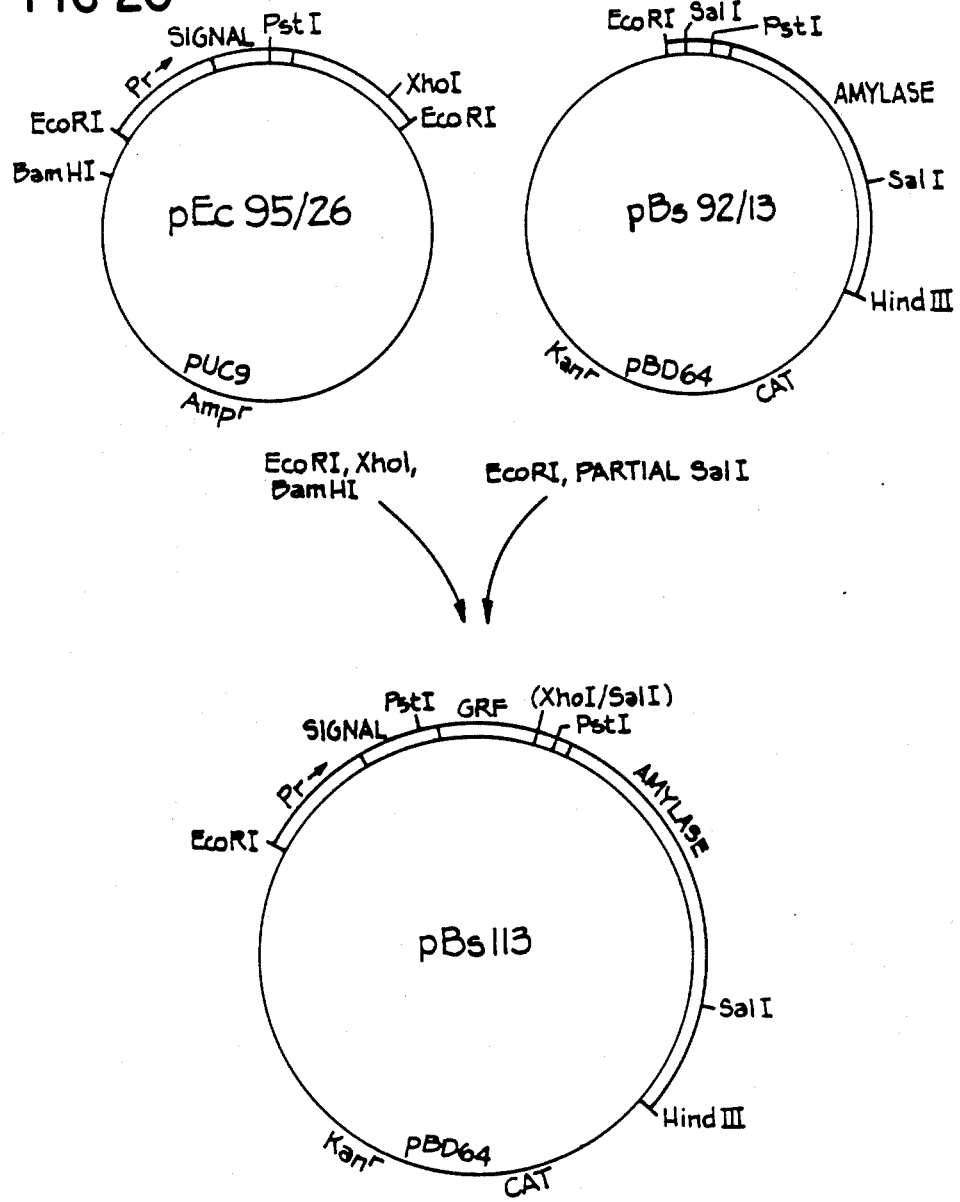

An additional vector of the invention, pBs113, is illustrated in FIG. 20, and its structure and construction described below.

Structure and Construction of pBs113

Figure 19:
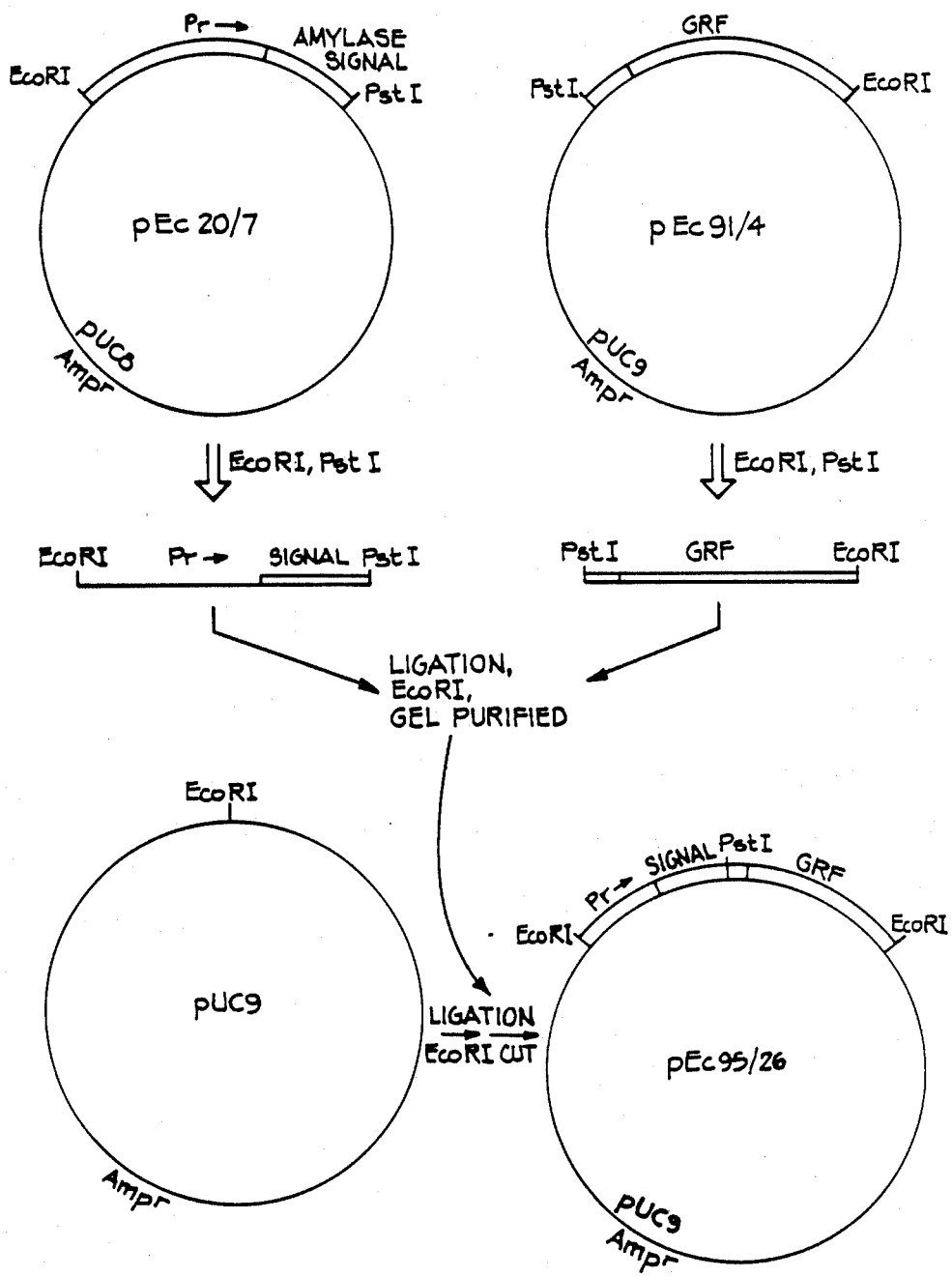
FIGS. 19 and 20 are diagrammatic representations of the structure and construction of α-amylase-GRF fusions.

FIGS. 19 and 20 are diagrammatic representations of the construction of pBs113, a vector in which a synthetic GRF gene depicted in FIG. 31 is inserted in the B. licheniformis α-amylase gene adjacent to the α-amylase signal sequence.

The α-amylase signal sequence was joined to the GRF gene with a synthetic DNA linker designed to create a "nature-identical" fusion of GRF to the signal sequence of α-amylase. The synthetic linker depicted in FIG. 31 was ligated to the approximately 130 bp EcoRI—Sau3A fragment encoding most of the synthetic GRF gene depicted in FIG. 31 at the Sau3A site and the fragment encoding GRF plus linker was subcloned between the PstI and EcoRI sites of pUC9 to yield plasmid pEc91/4.

Referring to FIG. 19, DNA encoding the signal sequence of α-amylase was isolated from pEC20/7 (FIG. 5) after treatment of pEC20/7 with EcoRI and PstI. This fragment was ligated to a PstI, EcoRI fragment of pEC91/4 containing the gene encoding GRF, and the resulting fragment treated with EcoRI and ligated to EcoRI-treated pUC9 to give pEC95/26.

Referring to FIG. 20, the C-terminus of the GRF gene in pEc95/26 was then fused to the α-amylase structural gene by treatment of pEc95/26 with EcoRI, BamHI, and XhoI and ligation of this mixture with pBs92/13 (containing the α-amylase structural gene) restricted with EcoRI and partially with SalI. The resulting plasmid, pBs113, has the GRF gene inserted into the α-amylase structural gene.

Secretion of GRF-α-amylase

The accumulated proteins secreted or retained by B. subtilis GP200 cells containing pBs113 were examined by Western blot analysis. In addition to a band similar in size to α-amylase, a higher molecular weight protein appeared to accumulate in the supernatant from the cells. This protein in the GP200 supernatant was the expected size for the GRF-α-amylase fusion protein (4–5 kd larger than α-amylase).

The secretion of the GRF-α-amylase fusion protein from B. subtilis cells was demonstrated by analyzing pulse-labelled proteins synthesized by GP200 cells containing pBs113 early in stationary phase. A measure of the stability of the fusion protein was then obtained by chasing with excess unlabelled amino-acid. Labelled fusion protein was isolated by immunoprecipitation with antibody to α-amylase and analyzed by gel electrophoresis.

Culture supernatants from pulse-labelled cells carrying pBs113 contained a predominant immunoreactive protein about 4–5 kdaltons larger than mature α-amylase. This protein was approximately the same molecular weight as the putative fusion protein detected by Western blot analysis. (A smaller proportion of label was found in a protein only sightly larger than normal α-amylase.) The appearance of the higher molecular weight species in culture supernatants occurred early in stationary phase, when there was minimal cell lysis and thus was a result of secretion and was not due to cell lysis.

Chasing with cold amino-acid led to an increase in the level of labelled proteins in the culture medium, indicating that proteins synthesized in the cell during labelling were eventually secreted into the medium. Since the quantity of label in the higher molecular weight extracellular protein increased after the chase, it is likely that the initial secreted product is the GRF-α-amylase fusion protein and that early on in a stationary-phase culture, this protein is secreted faster than it is degraded.

Figure 21:
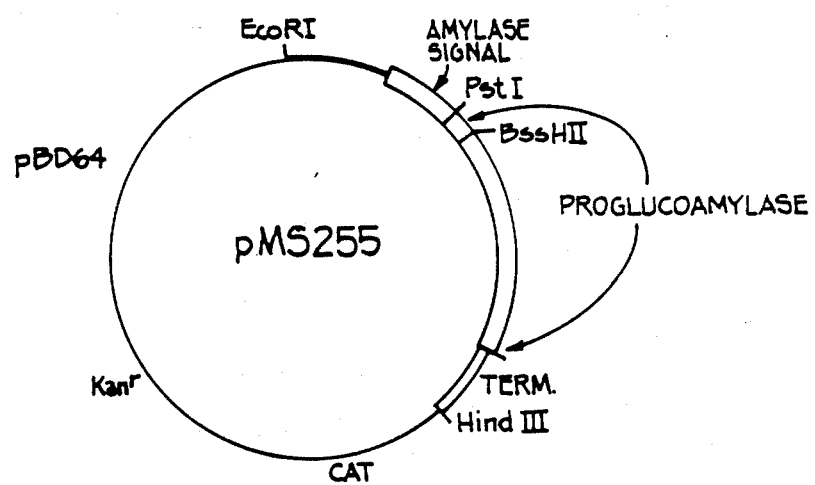
FIGS. 21 and 22 are diagrammatic representations of the structure and construction of an α-amylase signal-glucoamylase fusions.

An additional vector of the invention, pMS255, is illustrated in FIG. 21, and its structure and construction described below.

Structure and construction of pMS255

FIG. 21 is a diagrammatic representation of pMS255, a plasmid in which a gene for the proenzyme proglucoamylase is inserted adjacent to the α-amylase signal sequence.

The glucoamylase gene of A. niger is believed to be initially translated in a pre-pro form. A cDNA coding for A. niger glucoamylase has been cloned and partly sequenced (Yocum et al. U.S. Pat. Appln. Ser. No. 736,450, assigned to the same assignee as the present application, hereby incorporated by reference). A vector, pRD111, in E. coli, containing the glucoamylase gene, is on deposit in the American Type Culture Collection, Rockville, Md., and bears ATCC Accession No. 53123. This vector was deposited in accordance with the Budapest Treaty. The pre-pro-enzyme has a signal sequence of about 18 amino acid residues that is removed to produce proglucoamylase. The proglucoamylase molecule consists of mature glucoamylase of 616 residues with 6 additional amino acid residues on the amino terminus. These additional amino acids are released, probably by cleavage downstream from two basic residues, to form mature glucoamylase. Proglucoamylase in which one of the two basic residues (arginine) had been changes to a proline residue has been reported to retain full enzymatic activity.

Figure 22:
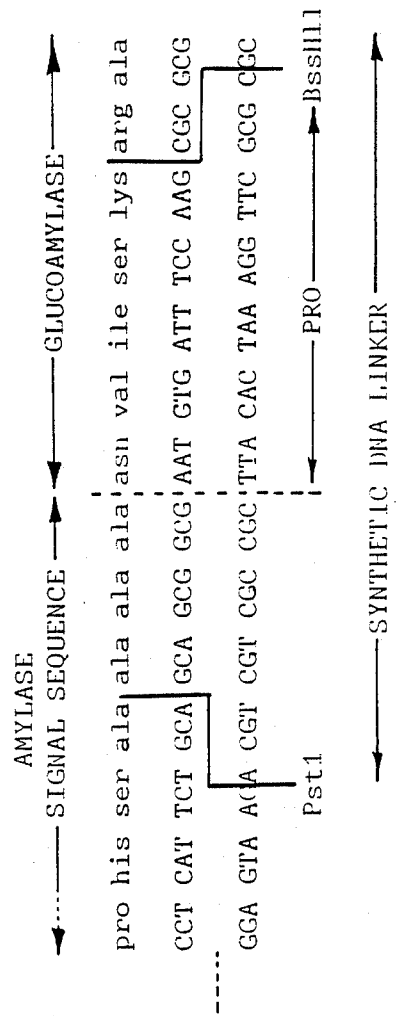

Plasmid pMS255 was designed to secrete proglucoamylase from B. subtilis. To achieve this, the promoter, ribosome binding site, and signal sequence of the glucoamylase gene were replaced with the expression controlling elements of the B. licheniformis α-amylase gene. A synthetic DNA linker (FIG. 22) was synthesized that would link the PstI site at the end of the α-amylase signal sequence to a BssHII site located at the junction of the pro- and mature portions of the glucoamylase gene. The linking sequence would also reconstitute the carboxy-terminus of the α-amylase signal sequence and the amino-terminus of the pro-glucoamylase protein (FIG. 22). The final construction (pMS255) shown in FIG. 21 contains a yeast transcription terminator located downstream from the glucoamylase sequence.

Secretion of proglucoamylase

Protease proficient (strain 1A289) and protease deficient (strain GP200) cells containing pMS255 were examined for their ability to secrete glucoamylase by colonyl immunoassay using antibody to glucoamylase as probe. Only protease deficient GP200 cells that contained the pro-glucoamylase gene in frame with the B. licheniformis α-amylase signal sequence synthesized an immunoreactive protein. Western blot analysis of the culture supernatants and cell extracts showed that a protein of about 68,000 daltons (the predicted size of non-glycosylated proglucoamylse) was secreted by the GP200 strain carrying plasmid pMS255. Four to five times more immunoreactive protein appeared to be accumulated by the cell than released into the culture medium. The low yield of proglucoamylase may reflect its release by cell lysis rather than by secretion.

Figure 30:
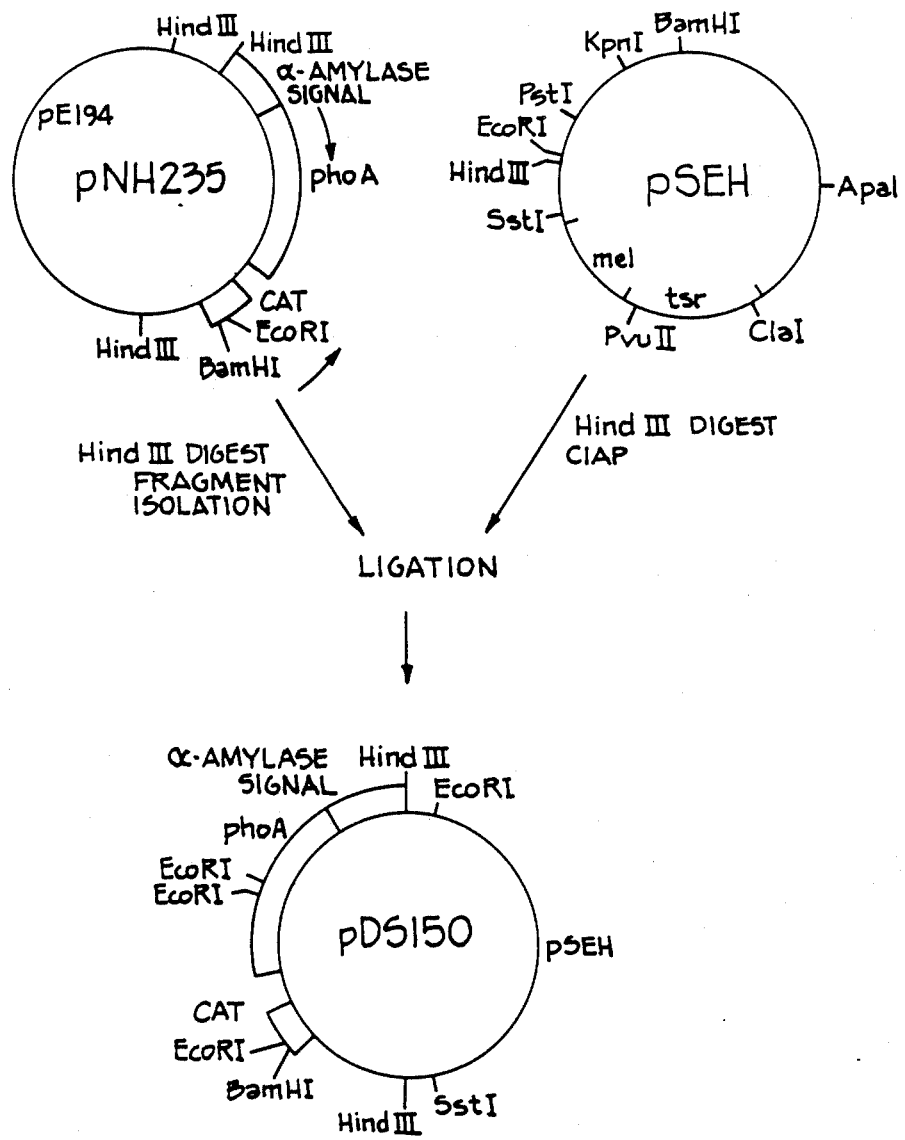
FIG. 30 is a diagrammatic representation of the structure and construction of an α-amylase signal-alkaline phosphatase fusion vector capable of replicating in Streptomyces.

An additional vector of the invention, pDS150, is illustrated in FIG. 30, and its structure and construction described below.

Structure and Construction of pDS150 pDS150 contains DNA encoding the B. licheniformis alpha-amylase signal sequence fused to the E. coli alkaline phosphatase gene which is then inserted into a high copy-number Streptomyces replicon.

FIG. 30 is a diagrammatic representation of the construction of pDS150. The Bacillus plasmid, pNH235, is a pE194 replicon and was the source of the DNA containing the α-amylase-alkaline phosphatase (amy-phoA) fusion. The fusion was originally constructed on plasmid pNH216 (described above; the sequence is given in FIG. 8). The Streptomyces plasmid pSEH (FIG. 30), used as the replicon in constructing pDS150, is a high copy-number plasmid derived from pIJ702 and contains a unique HindIII site for the insertion of DNA. (pIJ702 is described in Katz et al., J. Gen. Micro. 129: 2703-2714 (1983), and is available from the John Innes Institute, Norwich, England.)

Both pNH235 and pSEH were cut with HindIII. The 5.6 kb fragment from pNH235 containing the amy-phoA fusion was isolated and ligated to alkaline phosphatase-treated pSEH. Protoplasts of S. lividans strain 1326 were transformed with the ligation mixture. Transformants were selected on the basis of thiostrepton resistance and were further screened by restriction analysis for the presence of pDS150.

Secretion of Alkaline Phosphatase by Streptomyces

Secretion of alkaline phosphatase by Streptomyces lividans strain 1326 via the B. licheniformis alpha-amylase signal sequence was demonstrated by Western blot analysis. S. lividans cells containing pDS150 were grown in YEME medium for 4 days for analysis. Culture supernatants of those cells gave a positive antigenic response with a protein band migrating at approximately the same position as mature E. coli alkaline phosphatase.

Other Promoters

As mentioned above, the secretion vectors can employ promoter sequences other than that naturally associated with the B. licheniformis α-amylase signal-encoding sequence. Promoterless vectors containing the signal-encoding sequence preceded by unique restriction sites have been constructed, and have been used in conjunction with other promoters, for the screening of DNA fragments for promoter activity, as follows.

Promoterless Vectors

Figure 23:
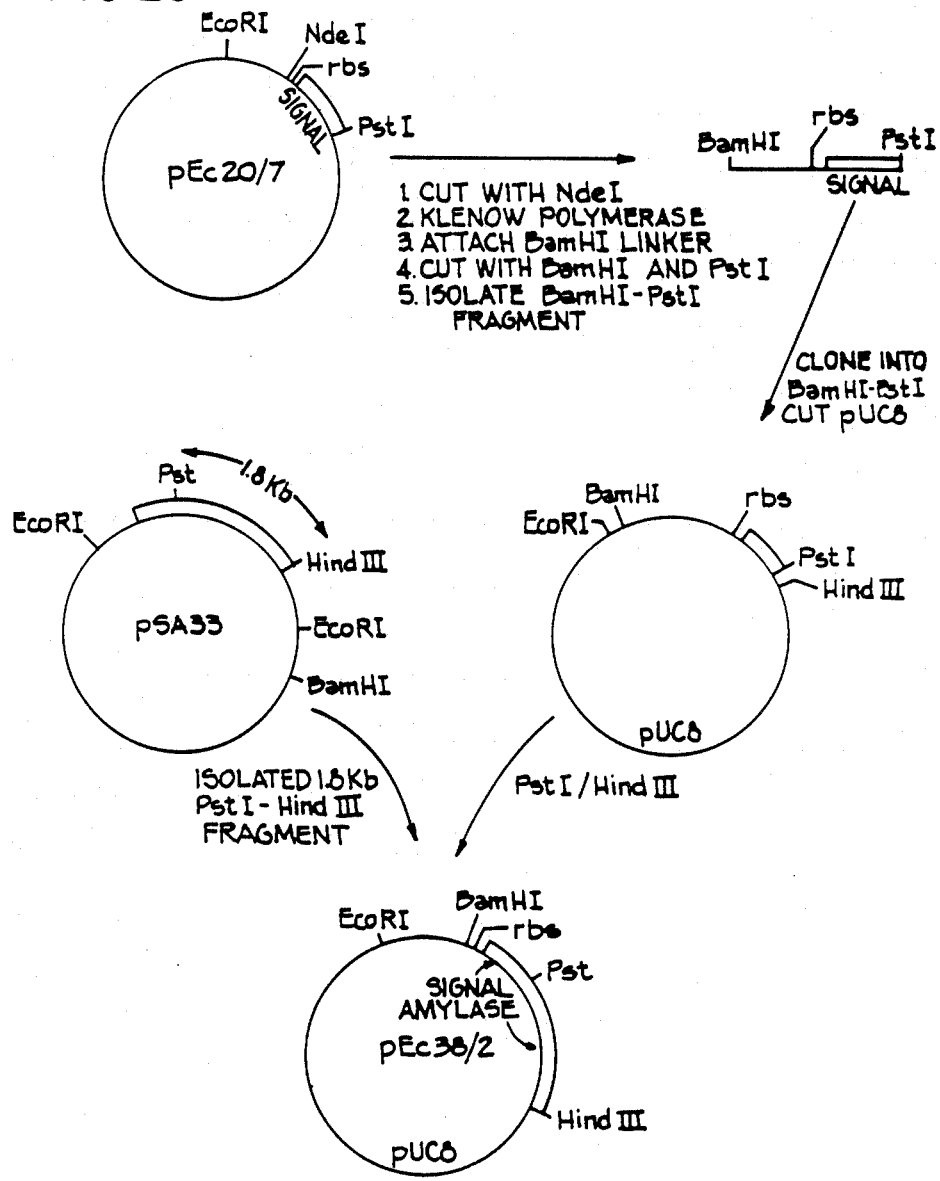
FIGS. 23–25 are diagrammatic representations of the construction of vectors, pEc38/2, pBs86/3, and pBs94/m5, respectively, containing promoterless B. licheniformis α-amylase genes with unique upstream restriction sites for the insertion of a desired promoter sequence.

Referring to FIG. 23, a BamHI linker was attached to the NdeI site of pEc20/7 (described earlier) just upstream from the DNA encoding the α-amylase ribosome binding site and signal sequence, and downstream from the α-amylase promoter, by cutting with NdeI, treating with Klenow polymerase, and then attaching the linker.

The 1.9 kb BamHI-HindIII fragment containing the DNA encoding the ribosome binding site, signal sequence and α-amylase was then subcloned into the E. coli plasmid pUC8 to produce the first promoterless plasmid, pEc38/2, as follows. First, the BamHI-PstI fragment from linkered pEc20/7 containing most, but not all, of the signal encoding sequence, was excised using BamHI and PstI. pUC8, containing the BamHI-PstI fragment, was then cut with PstI and HindIII. The B. licheniformis α-amylase gene, including the portion of the signal-encoding sequence missing from pEc20/7, was cut out of pSA33 (described earlier) as a 1.8 kb PstI-HindIII fragment and inserted into cut pUC8 containing the linkered signal sequence, to form pEc38/2.

Figure 24:
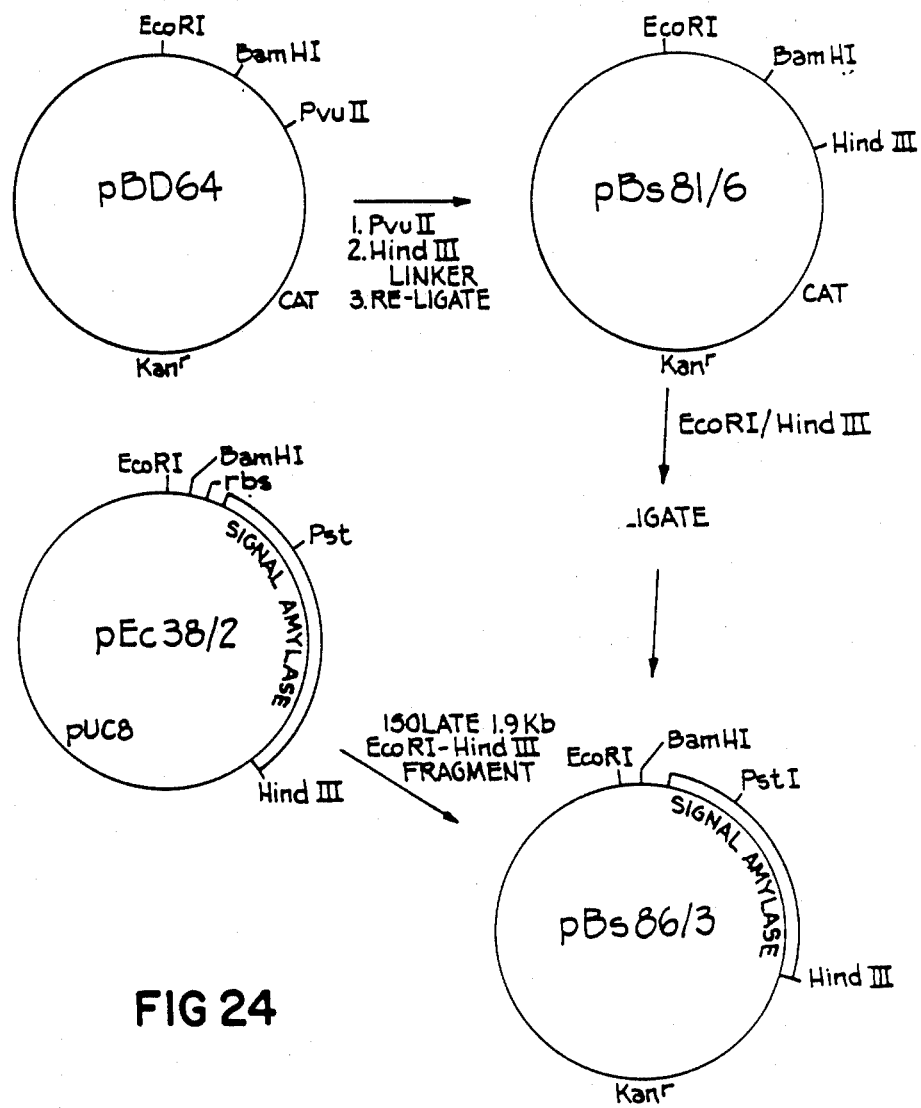

Referring to FIG. 24, a second promoterless plasmid pBs86/3 was constructed as follows. Plasmid pBD64 was cut with pvuII and a HindIII linker inserted to form pBs81/6 upon religation; pBs81/6 was then cut with EcoRI and HindIII, and the 1.9 kb EcoRI-HindIII α-amylase containing DNA fragment from pEc38/2 inserted to form pBs86/3.

Figure 25:
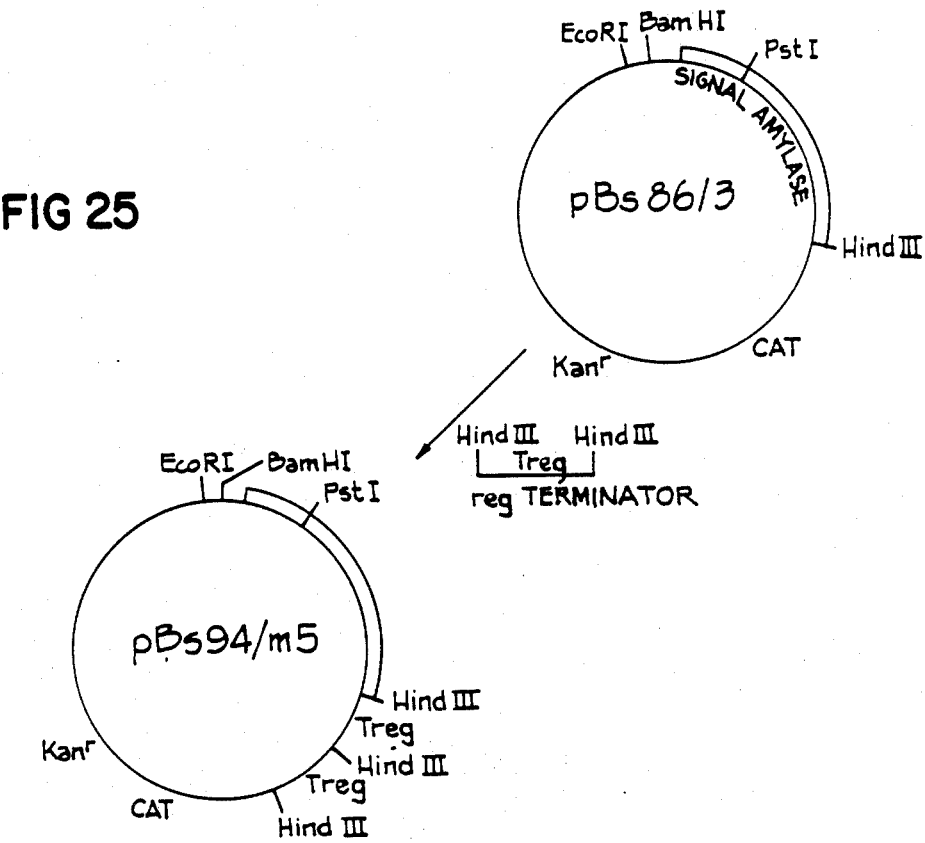

Referring to FIG. 25, a third promoterless plasmid, pBs94/m5, was derived from pBs86/3 by inserting 300 bp HindIII fragments containing the transcription terminator for the B. subtilis veg gene (described in Segall et al. (1977) Cell 11, 751) into the HindIII site of pBs86/3.

Figure 26:
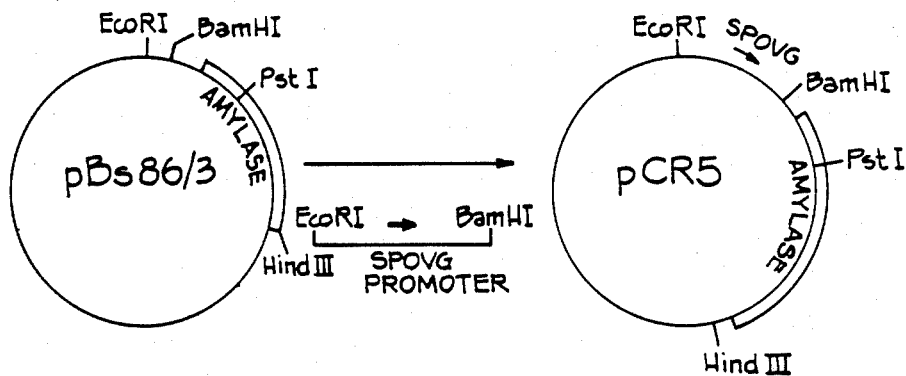
FIGS. 26 and 27 are diagrammatic representations of the insertion of the spoVG promoter into, respectively, pBs86/3 and pBs94/m5.
Figure 27:
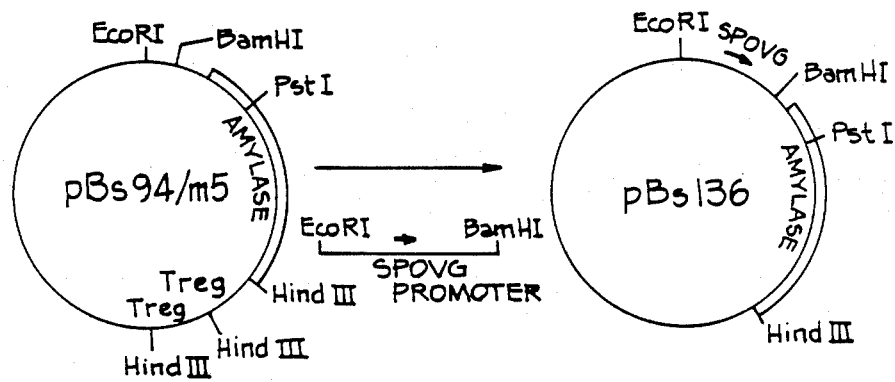
Figure 28:
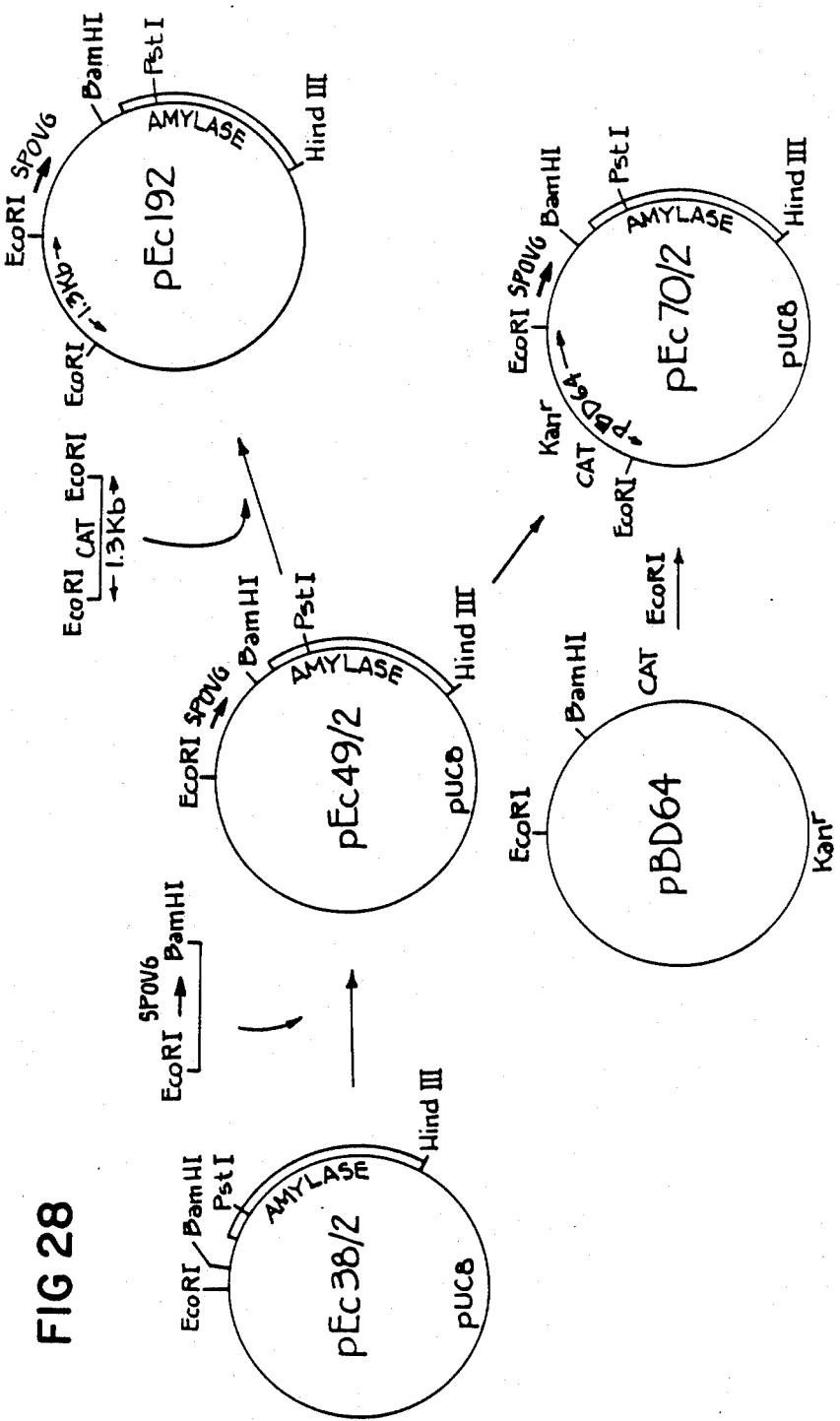
FIG. 28 is a diagrammatic representation of the construction of two vectors, pEc192 and pEc70/2, by the insertion of the spoVG promoter into pEc38/2.

Insertion of the spoVG Promoter pEc38/2, pBs86/3 and pBs94/5 all contain a promoterless α-amylase gene with unique RI and BamHI sites positioned just upstream of the putative α-amylase ribosome binding site. We introduced, using standard techniques, a 1.7 kb EcoRI-BamHI fragment containing the promoter for the sporulation gene spoVG (Moran et al. (1981) Cell 25, 783-791) into (i) pEc38/2 to produce pEc49/2; (ii) pBs86/3 to produce pCR5 and (iii) into pBs94/m5 to produce pBs136 (FIGS. 26-28).

While both pCR5 and pBs136 were capable of replicating in B. subtilis as plasmids, pEc49/2 contained only an E. coli replicon and could not replicate in B. subtilis. We therefore introduced at the EcoRI site of pEc49/2 (a) a copy of the Bacillus replicon pBD64 cut with EcoRI to produce the bi-functional replicon pEc70/2, and (b) a copy of the chloramphenicol gene from pC194 at the RI site of pEc38/2 to produce pEc192, a plasmid capable of replicating in E. coli as an autonomous replicon and in B. subtilis as a part of the Bacillus chromosome (FIG. 28).

pCR5, pBs136, pEc70/2 and pEc192 were all transformed into competent amylase-minus B. subtilis strain IA289. All transformants were shown to secrete large quantities of α-amylase as detected by the production of large clear halos on starch-agar plates and as measured by a liquid α-amylase assay. The production of α-amylase was comparable, and in most cases higher, than that of cells containing the α-amylase gene transcribed from the original *B. licheniformis* promoter.

Screening for Promoter Activity

The promoterless plasmids pBs86/3 and pBs94/5 can also be used to isolate new fragments of DNA exhibiting promoter activity. To demonstrate this, we cleaved DNA derived from *B. amyloliquefaciens* with the enzyme Sau3A, ligated the resulting pool of DNA fragments into BamHI cut pBs94/m5, and transformed the DNA mixture into competent amylase-minus *B. subtilis*. More than 10% of the resulting colonies, selected on nutrient agar plates containing chloramphenicol, contained fragments of *B. amyloliquefaciens* DNA that were capable of initiating transcription of the α-amylase gene to produce significant quantities of α-amylase.

The promoterless plasmids pBS94/m5 and pBs86/3 can therefore be used to isolate new promoters which may have useful properties not possessed by the *B. licheniformis* α-amylase promoter, e.g., a higher lever of expression, or regulated expression.

As discussed earlier the above-described plasmids, containing the *B. licheniformis* α-amylase gene, including regions encoding the ribosome binding site and signal sequence, can be used for the production and secretion of heterologous polypeptides. The promoter of choice is inserted into the vector, upstream from the ribosome binding site, and the gene encoding the desired heterologous polypeptide is inserted downstream from the signal-encoding sequence. The structural gene encoding α-amylase is either removed, using conventional techniques; or appropriate modification made in the vector so that a fusion protein containing both the heterologous polypeptide and α-amylase is not produced; or, as described above, a fusion protein may be produced intentionally.

The vectors of the invention are transformed into host Gram positive bacteria, preferably *B. subtilis*, using conventional techniques, and the vectors allowed to replicate, and express and secrete the heterologous polypeptide, in the host bacterial cells.

Replication in Host Cells

The vectors of the invention can replicate and be maintained in host cells by one of three mechanisms: (1) the vector can be derived from a plasmid, e.g., pBD64, pUB110, or pE194, which replicates autonomously in Bacillus cells and carries a gene for a selectable marker such as antibiotic resistance (see Gryczan (1982) in "The Molecular Biology of the Bacilli" (D. A. Dubnau, ed.) pp. 307-330, Academic Press, New York)); or (2) the vector can be derived from a phase, e.g., ρ11, φ105, or SPβ, which replicates in or lysogenizes Bacillus cells (Gryczan, id); or (3) the vector can be one which does not replicate autonomously in Bacillus cells but that carries DNA homologous with a region of the host cell chromosome so that the vector can integrate into the bacterial chromosome (see Haldenwang et al. (1980) J. Bact. 142 90–98; Zuber, P. and Losick, R. (1983) Cell 35 275–283).

If an integration vector also contains a selectable gene such as a drug-resistance marker (e.g., chloramphenicol resistance), selection can be used to amplify the vector in the chromosome (Young (1984) J. Gen. Micro. 130, 1613–1621). Some vectors can be maintained stably in the absence of drug-selection only when integrated into the bacterial chromosome.

Integration of Vectors into the Host Chromosome

In order to maintain recombinant plasmids in Bacillus and other Gram positive bacterial species, it is necessary to maintain a continuous selection against loss of the plasmid. In most cases this selection involves an antibiotic such as neomycin, chloramphenicol, or erythromycin. The presence of a gene on the plasmid that confers resistance to the drug ensures that only cells that contain a plasmid will grow. Continuous maintenance of drug selection in a commercial-scale process requires addition of the drug to the fermentation media. As this can be expensive or in other ways undesirable, it will in some instances be useful to integrate the vector into the host chromosome to prevent loss of the vector in a manner which does not require continuous selection.

Integration is achieved by means of a segment of vector DNA which is attached to the DNA construct which is required to be stably maintained, which segment is homologous to a region of DNA on the host chromosome.

When the DNA construction, which should be incapable of autonomous replication in the host, is then introduced into the host cells by transformation, the only way cells will retain the incoming DNA will be as a consequence of recombination between the homologous regions of DNA on the incoming DNA and host chromosome. (See Duncan et al. (1978) PNAS 75, 3664–3668; Haldenwang et al. (1980) J. Bact. 142, 90–98.)

We have demonstrated the effectiveness of this process by constructing a segment of recombinant DNA that will direct the secretion of α-amylase from *B. subtilis* in the absence of continuous drug selection.

Figure 29:
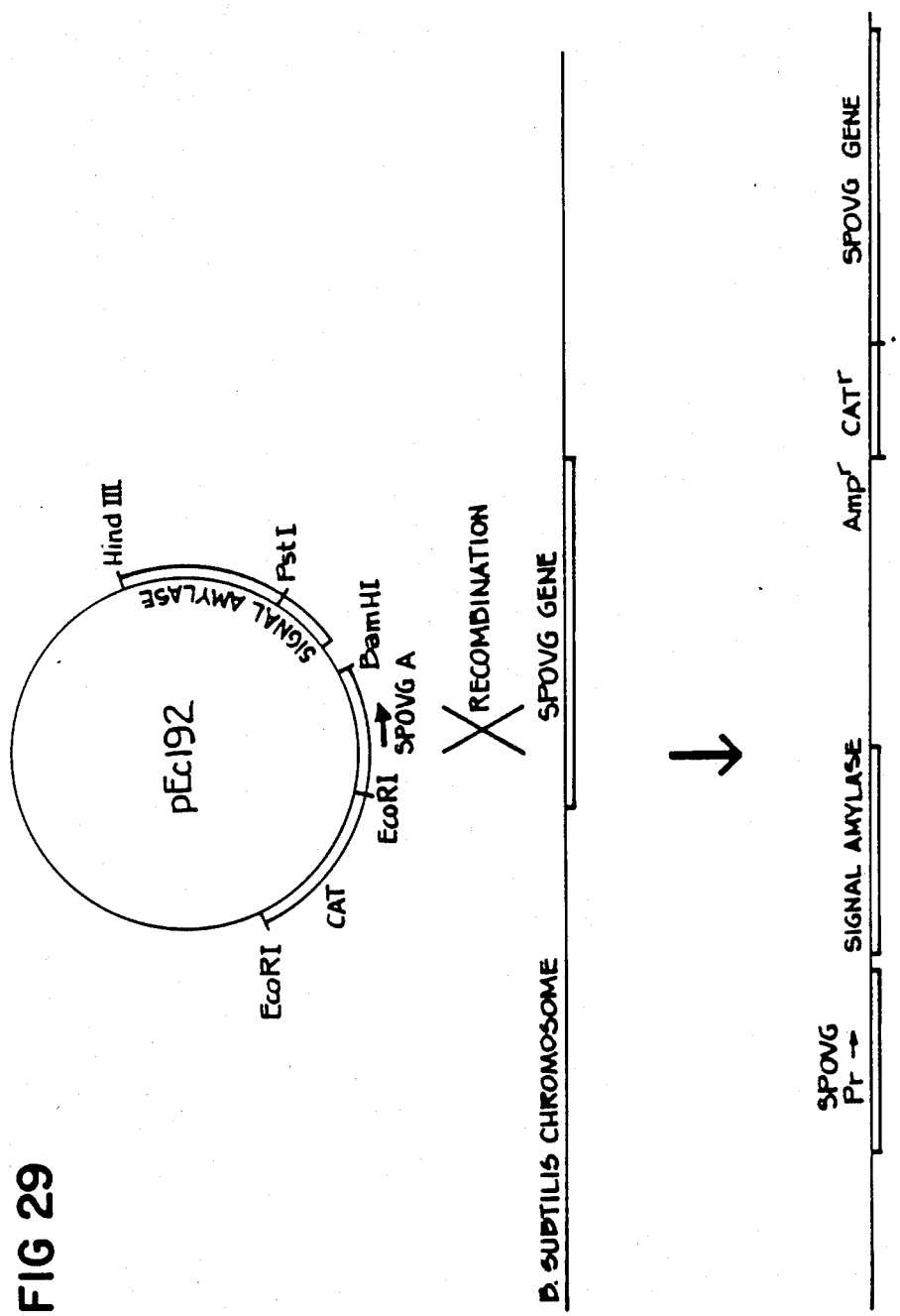
FIG. 29 is a diagrammatic representation of the integration of pEc192 into a Bacillus chromosome.

Plasmid pEc192, described above (FIG. 28), contains the gene for chloramphenicol resistance (originally from pC194), the spoVG DNA homologous with a region of the spoVG gene on the *B. subtilis* chromosome. pEc192 is not capable of autonomously replicating in *B. subtilis*. The mechanism by which pEc192 integrates into the *B. subtilis* chromosome is illustrated in FIG. 29.

pEc192 was transformed into a competent *B. subtilis* strain IA289 (amylase-deficient strain), and transformants containing the recombinant DNA were selected by plating on nutrient agar plates containing 5 μg/ml chloramphenicol. All the resulting drug resistant colonies were shown to be secreting α-amylase as indicated by the production of clear halos on agar plates containing starch. Cells containing a higher number of copies of the recombinant DNA were obtained by streaking the cells onto plates containing increasing levels of the drug (up to 90–120 μg/ml). To demonstrate that additional copies of the recombinant DNA were obtained, total DNA, prepared from cells that could grow on high levels of drug, was digested with HindIII or EcoRI, analyzed by gel electrophoresis, and compared to the similarly digested DNA derived from an initial "low-copy" transformant and DNA derived from a plasmid containing an autonomously replicating plasmid. Multiple copies of the recombinant DNA, seen as intensely stained DNA bands above a heterogeneous background of chromosomal DNA, were observed from DNA isolated from the highly drug resistant strain but not from DNA isolated from the low drug resistant transformant. The intensity of these bands was comparable to that seen for DNA derived from the autonomously replicating plasmid, demonstrating that the copy number of the integrated DNA was comparable to the copy number of the autonomously replicating plasmid.

The enhanced stability of the integrated versus autonomously replicating DNA was demonstrated by growing cells containing either an autonomously replicating plasmid or integrated DNA for a number of generations in the absence of drug selection and testing for the retention of the recombinant DNA by screening for resistance to drug and production of α-amylase. As shown in the Table, below, cells containing the α-amylase and chloramphenicol resistance genes on an autonomously replicating plasmid lost their drug resistance and α-amylase production at a much higher rate than cells containing the two genes integrated into the chromosome.

TABLE

Stability of Cloned α-Amylase Gene on Plasmids or Amplified in the Chromosome Number of Colonies

| PLASMID | TOTAL NUMBER | $Cm^r$ (all amy+) | $CM^s$ (all amy−) | LOSS OF DRUG RESISTANCE |
|---------|--------------|-------------------|-------------------|-------------------------|
| pSA33   | 259          | 93                | 166               | 64%                     |
| pBs136  | 270          | 29                | 241               | 89%                     |
| pBs219  | 227          | 227               | 0                 | 0.4%                    |

The drug resistance and homologous region component of pEc192 could be replaced with other segments of DNA with comparable functions and properties and, as discussed above, the vector can be used to secrete desired polypeptides.

DEPOSIT pNH218 in *B. subtilis* has been deposited with the American Type Culture Collection and given ATCC Accession Number 53063. This culture will be maintained for 30 years, 5 years after the request for any one strain, or until the end of the term of the patent issued, whichever is the longer. Applicants' assignee, BioTechnica International, Inc., acknowledges its responsibility to replace this culture should it die before the end of the term of a patent issued hereon, and its responsibility to notify the ATCC of the issuance of such a patent, at which time the deposit will be made irrevocably available to the public. Until that time the deposit will be made available to the Commissioner of Patents under the terms of 37 CFR §1.14 and 35 USC §112.

Other embodiments are within the following claims.

We claim:

1. A vector comprising
   the secretory signal-encoding sequence of the *Bacillus licheniformis* α-amylase gene;
   upstream from said signal-encoding sequence, a promoter sequence and a ribosome binding site sequence, transcription of said signal-encoding sequence being under the control of said promoter sequence; and
   downstream from said signal-encoding sequence, a site for the insertion into said vector of a heterologous DNA sequence, in reading frame with said signal-encoding sequence.

2. The vector of claim 1, said site being located in a DNA sequence encoding a peptide or polypeptide different from the peptide or polypeptide encoded by said heterologous DNA sequence, so that said vector encodes a fusion polypeptide.

3. The vector of claim 2, said different polypeptide being *B. licheniformis* α-amylase.

4. The vector of claim 3, said site being at the C-terminus of the DNA sequence encoding said α-amylase.

5. The vector of claim 2, said site being located at the 3' end of said DNA sequence encoding a peptide or polypeptide different from the peptide or polypeptide encoded by said heterologous DNA sequence.

6. The vector of claim 1 wherein said promoter and ribosome binding site sequences are naturally occurring Bacillus promoter and ribosome binding site sequences.

7. A Gram positive bacterial cell transformed with the vector of claim 1.

8. The bacterial cell of claim 7; said cell being of the genus Bacillus.

9. The bacterial cell of claim 8, said cell being *B. subtilis*.

10. The bacterial cell of claim 7, said cell being of the genus Streptomyces.

11. The bacterial cell of claim 7 wherein said vector further comprises a DNA region homologous with a DNA region of the chromosome of said host bacterial cell, said vector being integrated into said chromosome at said region of homology.

12. A Gram-negative bacterial cell transformed with the vector of claim 1.

13. The bacterial cell of claim 12, said cell being *E. coli*.

14. The vector of claim 1, further comprising DNA capable of causing said vector to replicate autonomously in a Bacillus cell.

15. The vector of claim 1, further comprising DNA capable of causing said vector to integrate into the host chromosome and be amplified.

16. The vector of claim 1, further comprising DNA capable of causing said vector to replicate autonomously in a Streptomyces cell.

17. The vector of claim 1, further comprising DNA capable of causing said vector to replicate autonomously in an *E. coli* cell.

18. A method of producing a heterologous polypeptide in a bacterial cell comprising
    transforming said cell with a vector comprising a DNA sequence encoding said heterologous polypeptide, said DNA sequence being positioned downstream from a DNA sequence encoding the secretory signal encoding sequence of the *Bacillus licheniformis* α-amylase gene, said DNA encoding said secretory signal being positioned downstream from a promoter sequence and a ribosome binding site sequence capable of functioning in said bacterial cell, transcription of said DNA sequence encoding said signal sequence and said heterologous polypeptide-encoding sequence being under the control of said promoter sequence, said secretory signal encoding sequence and said heterologous polypeptide-encoding sequence together encoding a polypeptide having a signal sequence capable of effecting the secretion from said cell of said heterologous polypeptide,
    culturing said cell to produce and secrete said heterologous polypeptide from said cell, and
    recovering said secreted heterologous polypeptide.

19. A Streptomyces cell transformed with a vector comprising
    a DNA sequence encoding the secretory signal-encoding sequence of the *Bacillus licheniformis* α-amylase gene;
    upstream from said signal-encoding sequence, a promoter sequence and a ribosome binding site sequence, transcription of said signal-encoding sequence being under the control of said promoter sequence; and downstream from said signal-encoding sequence, a site for the insertion into said vector of a heterologous DNA sequence, in reading frame with said signal-encoding sequence, said heterologous DNA sequence being inserted at said site, and transcription of said heterologous DNA sequence being under the control of said promoter sequence.

* * * * *